(12) United States Patent
Sardari et al.

(10) Patent No.: US 12,064,575 B2
(45) Date of Patent: *Aug. 20, 2024

(54) CATHETER SHEATH DEVICES AND METHODS OF OPERATING CATHETER SHEATH DEVICE

(71) Applicant: KARDIUM INC., Burnaby (CA)

(72) Inventors: Ashkan Sardari, North Vancouver (CA); Ian Garben, Burnaby (CA); Calvin Dane Cummings, Surrey (CA); Saar Moisa, Vancouver (CA); John Andrew Funk, Delta (CA)

(73) Assignee: KARDIUM INC., Burnaby (CA)

( * ) Notice: Subject to any disclaimer, the term of this patent is extended or adjusted under 35 U.S.C. 154(b) by 64 days.

This patent is subject to a terminal disclaimer.

(21) Appl. No.: 17/846,416

(22) Filed: Jun. 22, 2022

(65) Prior Publication Data

US 2022/0323722 A1 Oct. 13, 2022

Related U.S. Application Data

(63) Continuation of application No. 17/564,388, filed on Dec. 29, 2021, now Pat. No. 11,406,797, which is a
(Continued)

(51) Int. Cl.
*A61M 25/06* (2006.01)
(52) U.S. Cl.
CPC . *A61M 25/0662* (2013.01); *A61M 2025/0681* (2013.01)
(58) Field of Classification Search
CPC .......... A61M 25/0028; A61M 25/0097; A61M 25/0662; A61M 2025/0681
See application file for complete search history.

(56) References Cited

U.S. PATENT DOCUMENTS 4,127,141 A * 11/1978 Ledonne ............... F16L 55/124
137/321
4,306,705 A * 12/1981 Svensson .............. A61F 5/4405
604/905
(Continued)

FOREIGN PATENT DOCUMENTS

CA    2877699 A1    2/2014
FR    2284303 A1 *  4/1976
(Continued)

OTHER PUBLICATIONS

International Search Report issued in Intl. Appln. No. PCT/CA2019/050381 mailed Jun. 5, 2019.
(Continued)

*Primary Examiner* — Nathan R Price
*Assistant Examiner* — Mark A Igel
(74) *Attorney, Agent, or Firm* — ROSSI, KIMMS & McDOWELL LLP

(57) ABSTRACT

A catheter sheath device may include an elongate member and a moveable member. The elongate member may include a first lumen, and the moveable member may include a second lumen. The moveable member may be physically coupled to a portion of the elongate member to permit relative movement therebetween. A first relative movement between the moveable member and a portion of the elongate member may cause the second lumen to be positioned at a first location that permits delivery of at least a portion of a catheter into the second lumen but not into the first lumen from the second lumen. A second relative movement between the moveable member and the portion of the elongate member may cause the second lumen to be positioned at a second location that permits delivery of the at least the portion of the catheter through both the second lumen and the first lumen.

24 Claims, 14 Drawing Sheets

Related U.S. Application Data continuation of application No. 16/777,248, filed on Jan. 30, 2020, now Pat. No. 11,247,026, which is a continuation of application No. 16/535,471, filed on Aug. 8, 2019, now Pat. No. 10,589,069, which is a continuation of application No. PCT/CA2019/050381, filed on Mar. 27, 2019.

(60) Provisional application No. 62/669,594, filed on May 10, 2018.

(56) References Cited

U.S. PATENT DOCUMENTS

| | | | | |
|---|---|---|---|---|
| 4,576,199 | A * | 3/1986 | Svensson | F16K 27/044 604/905 |
| 4,745,907 | A | 5/1988 | Russel, Jr. et al. | |
| 4,968,309 | A | 11/1990 | Andersson | |
| 5,454,792 | A | 10/1995 | Tennican et al. | |
| 5,755,894 | A * | 5/1998 | Bowman | A61B 1/121 134/22.12 |
| 5,951,581 | A * | 9/1999 | Saadat | A61B 18/148 604/22 |
| 6,514,261 | B1 | 2/2003 | Randall et al. | |
| 6,641,564 | B1 * | 11/2003 | Kraus | A61M 25/065 604/110 |
| 6,932,795 | B2 * | 8/2005 | Lopez | A61M 39/045 604/249 |
| 7,137,974 | B2 * | 11/2006 | Almasian | A61M 39/14 604/905 |
| 7,708,714 | B2 * | 5/2010 | Connell | A61M 1/282 604/30 |
| 7,828,269 | B2 * | 11/2010 | Iversen | F16K 3/262 604/323 |
| 9,033,953 | B2 * | 5/2015 | Felber | A61M 1/75 604/74 |
| 9,452,016 | B2 | 9/2016 | Moisa et al. | |
| 9,528,649 | B2 * | 12/2016 | Aoki | F16L 37/44 |
| 11,247,026 | B2 * | 2/2022 | Sardari | A61M 25/0097 |
| 2002/0007152 | A1 * | 1/2002 | Hermann | A61B 17/3462 604/167.04 |
| 2003/0032922 | A1 * | 2/2003 | Moorehead | A61M 25/0631 604/110 |
| 2005/0096647 | A1 * | 5/2005 | Steinke | A61B 18/1815 606/41 |
| 2008/0200791 | A1 * | 8/2008 | Simpson | C12Q 1/006 600/365 |
| 2009/0270815 | A1 * | 10/2009 | Stamp | A61M 39/24 604/249 |
| 2013/0345673 | A1 | 12/2013 | Ferreri et al. | |
| 2014/0236275 | A1 * | 8/2014 | Thompson | A61F 2/95 623/1.11 |
| 2016/0166821 | A1 * | 6/2016 | Weiss | A61M 39/0613 604/164.02 |
| 2016/0220741 | A1 | 8/2016 | Garrison et al. | |
| 2018/0264225 | A1 | 9/2018 | Sardari et al. | |
| 2018/0264230 | A1 | 9/2018 | Funk et al. | |
| 2018/0296233 | A1 | 10/2018 | Schwager | |
| 2022/0008690 | A1 | 1/2022 | Sardari | |

FOREIGN PATENT DOCUMENTS

| | | | | |
|---|---|---|---|---|
| FR | 2284303 | A1 | 4/1976 | |
| GB | 1482857 | | 8/1977 | |
| WO | 9908931 | A1 | 2/1999 | |
| WO | 2007109257 | A2 | 9/2007 | |
| WO | WO-2007109257 | A2 * | 9/2007 | .......... A61B 17/221 |
| WO | 2015089649 | A1 | 6/2015 | |
| WO | WO-2015089649 | A1 * | 6/2015 | ......... A61B 18/1492 |
| WO | 2017070801 | A1 | 5/2017 | |
| WO | 2017100902 | A1 | 6/2017 | |
| WO | 2017124169 | A1 | 7/2017 | |
| WO | 2019213742 | A1 | 11/2019 | |

OTHER PUBLICATIONS

Written Opinion issued in Intl. Appln. No. PCT/CA2019/050381 mailed Jun. 5, 2019.

International Search Report issued in Intl. Appln. No. PCT/CA2016/000298 mailed Feb. 20, 2017.

Written Opinion issued in Intl. Appln. No. PCT/CA2016/000298 mailed Feb. 20, 2017.

Mounsey. "A novel multielectrode combined mapping and ablation basket catheter. A future player in the atrial fibrillation ablation space?" Journal of Cardiovascular Electrophysiology. 2017:1-2.

Kottkamp et al. "Global multielectrode contact mapping plus ablation with a single catheter: Preclinical and preliminary experience in humans with atrial fibrillation." Journal of Cardiovascular Electrophysiology. 2017:1-10.

Notice of Allowance received in U.S. Appln No. U.S. Appl. No. 16/535,471 mailed Nov. 27, 2019.

Office Action issued in U.S. Appl. No. 15/986,188 mailed Jan. 28, 2021.

Amendment filed in U.S. Appl. No. 15/986,188 on Apr. 22, 2021.

Notice of Allowance issued in U.S. Appl. No. 15/986,188 mailed Aug. 11, 2021.

Notice of Allowance issued in copending U.S. Appl. No. 17/564,388 mailed May 3, 2022.

Office Action issued in copending U.S. Appl. No. 16/777,248 mailed Jul. 27, 2021.

Amendment filed in copending U.S. Appl. No. 16/777,248 on Oct. 19, 2021.

Notice of Allowance issued in copending U.S. Appl. No. 16/777,248 mailed Dec. 10, 2021.

Extended European Search Report issued in European Application No. 19799136.7 mailed Jan. 12, 2022.

Office Action issued in copending U.S. Appl. No. 17/485,880 mailed Nov. 8, 2022.

Amendment filed in copending U.S. Appl. No. 17/485,880 on Nov. 16, 2022.

* cited by examiner

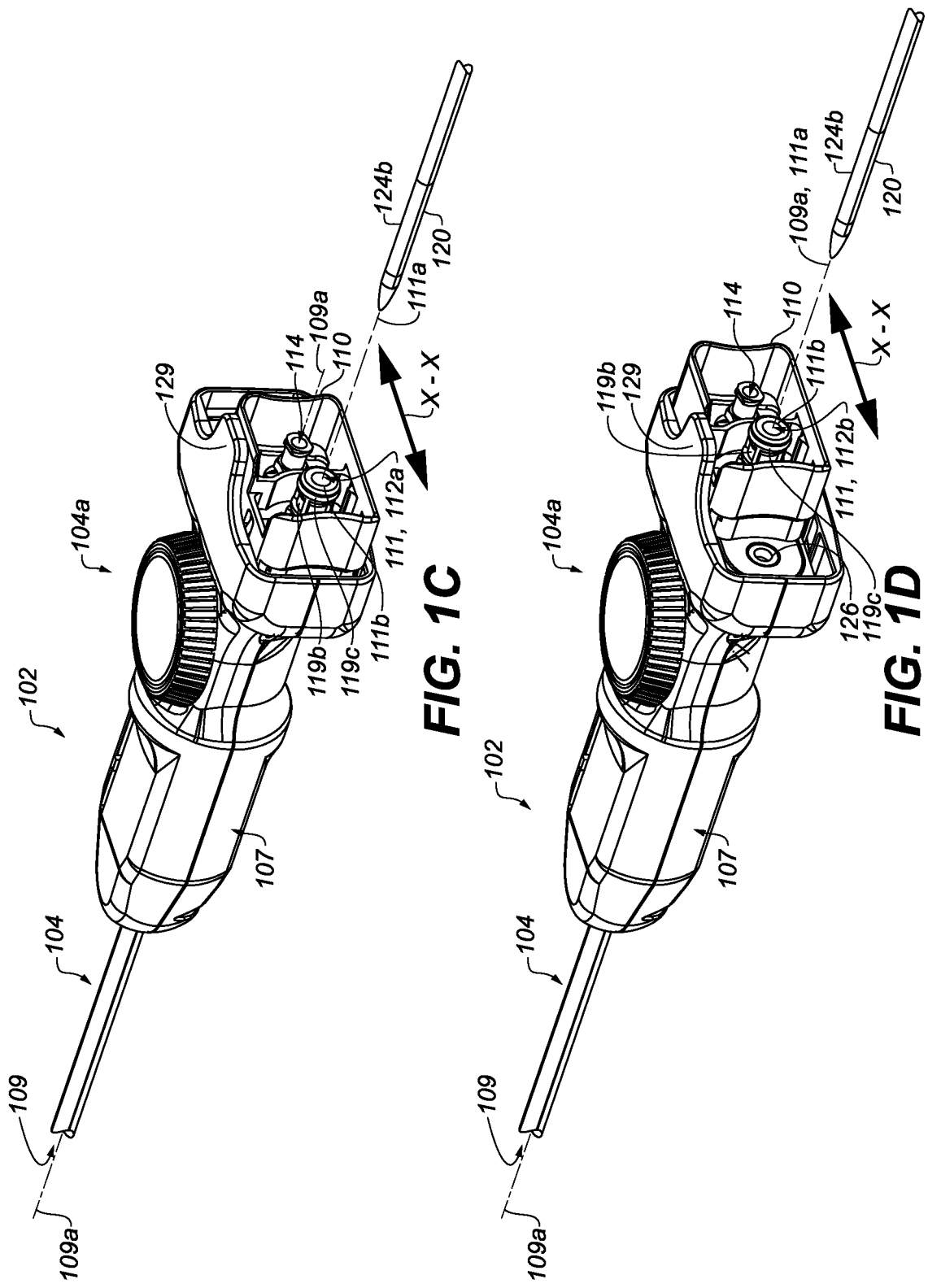

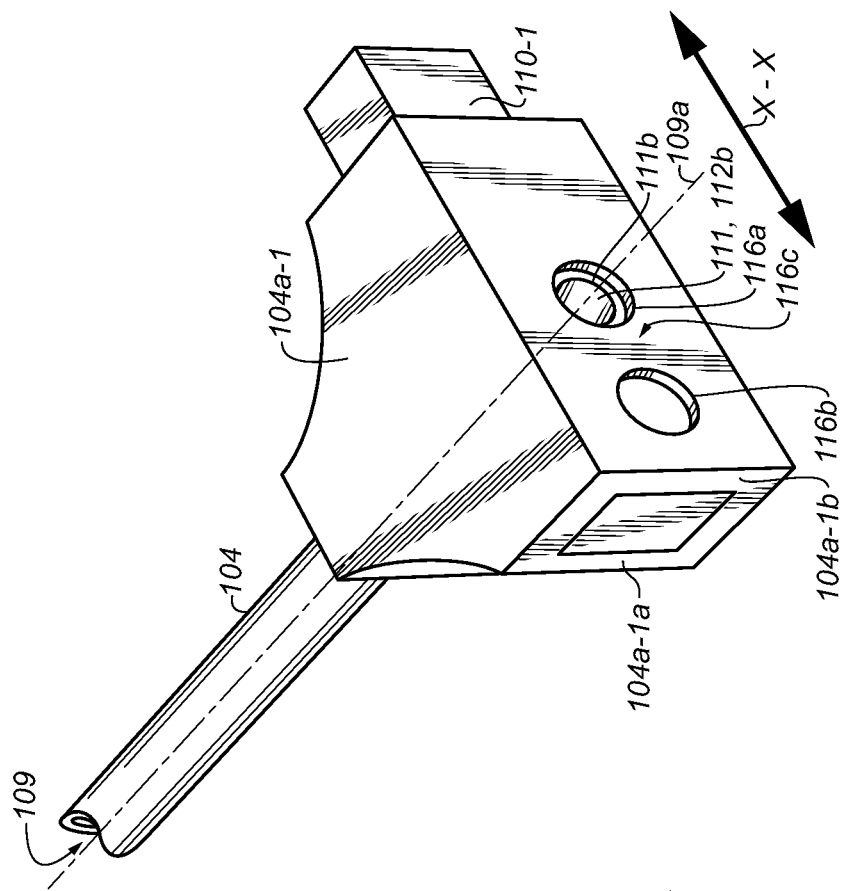
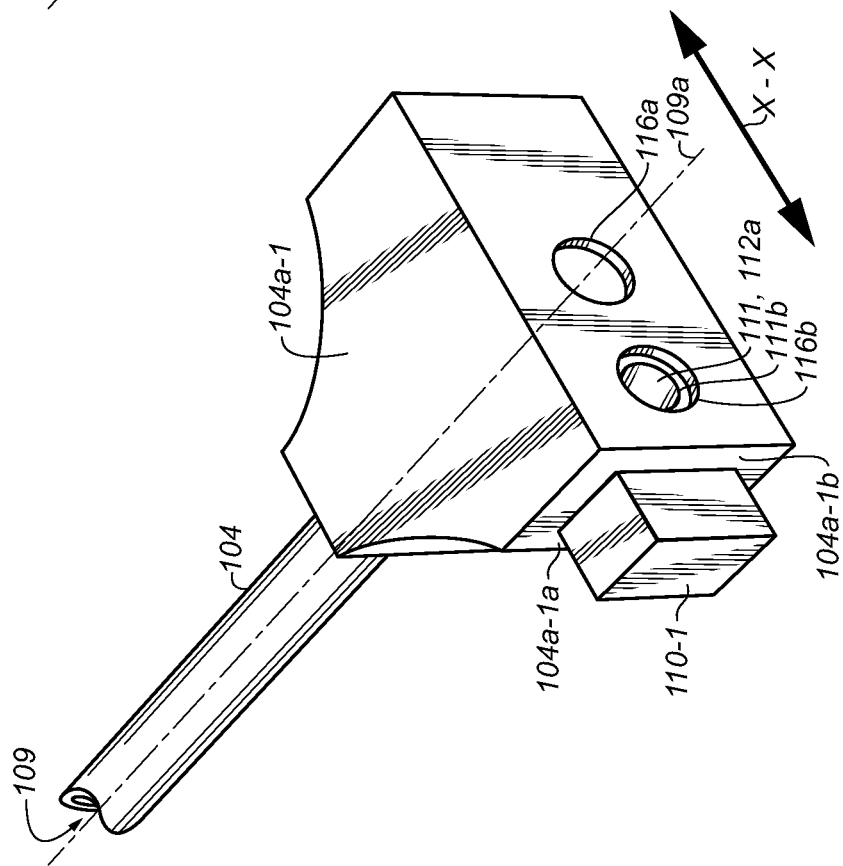
FIG. 2A
FIG. 2B

CATHETER SHEATH DEVICES AND METHODS OF OPERATING CATHETER SHEATH DEVICE

CROSS-REFERENCE TO RELATED APPLICATIONS

This application is a continuation of U.S. patent application Ser. No. 17/564,388, filed Dec. 29, 2021, now U.S. Pat. No. 11,406,797 issued Aug. 9, 2022, which is a continuation of U.S. patent application Ser. No. 16/777,248, filed Jan. 30, 2020, now U.S. Pat. No. 11,247,026, issued Feb. 15, 2022, which is a continuation of U.S. patent application Ser. No. 16/535,471, filed Aug. 8, 2019, now U.S. Pat. No. 10,589,069, issued Mar. 17, 2020, which is a continuation of International Application No. PCT/CA2019/050381, filed Mar. 27, 2019, which claims the benefit of U.S. Provisional Application No. 62/669,594, filed May 10, 2018, the entire disclosure of each of these applications is hereby incorporated herein by reference.

TECHNICAL FIELD

Aspects of this disclosure generally are related to catheter sheath devices and methods of operating a catheter sheath device. In some embodiments, catheter sheath devices and methods of operating a catheter sheath device are suitable for safely and efficiently flushing a catheter or one or more lumens of undesired fluid, such as air.

BACKGROUND

Cardiac surgery was initially undertaken using highly invasive open procedures. A sternotomy, which is a type of incision in the center of the chest that separates the sternum, was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications, and recovery time. However, the use of intravascular or percutaneous technologies also raises some particular challenges. Medical devices used in intravascular or percutaneous surgery need to be deployed via catheter systems, which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During various procedures, health care providers create specific patterns of lesions in the left or right atria to block various paths taken by the spurious electrical signals. Such lesions were originally created using incisions, but are now typically created by ablating the tissue with various techniques including radio-frequency (RF) energy, microwave energy, laser energy, and cryogenic techniques. The procedure is performed with a high success rate under the direct vision that is provided in open procedures but is relatively complex to perform intravascularly or percutaneously because of the difficulty in creating the lesions in the correct locations.

Preparation of catheter device systems for subsequent delivery through a bodily opening leading to a bodily cavity (e.g., as required by some percutaneous or intravascular procedures) may require that various undesired fluids (e.g., air) be purged or otherwise removed from portions of the systems prior to insertion into the body. Failure to do so may allow for a transfer of at least some of the undesired fluids to within the body, which may, in turn, result in various undesired outcomes (e.g., the formation of various air embolisms). Various catheter device systems employ various features that can act as fluid traps from which undesired fluid can be difficult to remove therefrom. For example, various lumens comprised by various catheter device systems may act as fluid traps.

In this regard, FIG. 7A is a schematic representation that shows at least part of a conventional catheter system that includes a catheter sheath 812 including a lumen that provides a passageway for a catheter (e.g., dilator catheter 800) delivered through a bodily opening during a medical procedure. In this regard, the catheter sheath (e.g., 812) is a member that is inserted into the body to shield the body from potential damage that may be caused by the delivery of a catheter introduced into the lumen of the catheter sheath. The catheter can take various forms. For example, the catheter can be an introducer or dilator (e.g., dilator catheter 800). The catheter (e.g., dilator catheter 800) is typically inserted through the lumen of the catheter sheath 812 from the proximal end 812a of the catheter sheath 812 to the distal end 812b of the catheter sheath 812. A tapered or point-like end 813 of the dilator catheter 800 typically protrudes from the distal end 812b of the catheter sheath 812 in a state in which the dilator catheter 800 is operably inserted into the lumen of the catheter sheath 812. The dilator catheter 800 and catheter sheath 812 assembly may then be advanced through the bodily opening with the tapered or protruding point-like end 813 of the dilator catheter 800 dilating or enlarging various parts of the bodily opening to facilitate the advancement of the assembly through the bodily opening. In some cases, the dilator catheter 800 and catheter sheath 812 assembly is advanced over a previously deployed guidewire to help guide the assembly to a desired location within the body of the patient. Once the assembly has been successfully delivered through the bodily opening to the desired location within the body, the dilator catheter 800 (and the guide wire if employed) is pulled out of the catheter sheath 812 leaving the catheter sheath 812 behind in the bodily opening. Each of one or more additional catheters (e.g., treatment or diagnostic catheters) or other medical instruments may then be advanced through the lumen of the catheter sheath 812 to the desired location within the body.

As discussed above, undesired fluid (e.g., air) may be trapped or otherwise present, for example, in the lumen of the catheter sheath 812, at least before or after the insertion of the catheter (e.g., dilator catheter 800) into the lumen. This undesired fluid requires removal (e.g., to avoid introducing the undesired fluid into the body) prior to advancement of the assembly of the dilator 800 and catheter sheath 812 through the bodily opening. Conventional catheter systems attempt to flush the undesired fluid by introducing a benign fluid, such as saline, into the region of the lumen of the catheter sheath 812 to flush the lumen of the undesired fluid. The introduction of fluid (e.g., saline) into the lumen of the catheter sheath 812 to remove the undesired fluid therefrom may occur at least before the insertion of the catheter (e.g., dilator catheter 800) into the lumen or after the insertion of the catheter (e.g., dilator catheter 800) into the lumen.

FIG. 7B shows a typical flushing procedure employed by conventional catheter systems. A source 802 of benign flushing fluid 804 (e.g., saline) is fluidically connected to the catheter sheath 812 at a location at least proximate the proximal end 812a (e.g., at supply connector 812c) to attempt to flush a region of the lumen between the dilator catheter 800 and the catheter sheath 812. It is noted that conventional flushing systems flush proximally (near proximal end 812a) toward distally (toward distal end 812b), because the supply connector 812c for the benign flushing fluid is provided proximally and not distally on the catheter member. In conventional flushing systems, a distal supply connector (e.g., a distal connector located proximate the distal end 812b of catheter sheath 812 rather than proximate proximal end 812a) would interfere with the introduction of the catheter member into the bodily opening and is therefore not employed. It is noted that even if the lumen of the catheter sheath 812 is filled with the benign flushing fluid, the introduction of the dilator or other catheter into the lumen may introduce undesired fluid into the lumen of the catheter sheath 812, thereby further complicating the flushing procedure.

As minimally invasive medical procedures are becoming more prevalent and use more complex catheter-based devices is increasing, a greater awareness for safety is materializing, leading to a greater sensitivity to air bubble ingress into the body (e.g., vascular system). The known art consists of passive and active radial seals that attempt to seal the lumen of the catheter sheath 812 against the outer circumference of the dilator catheter 800 (e.g., during vascular access and catheter sheath placement), and to seal against the outer circumference of a treatment or diagnostic catheter interchanged with the dilator catheter 800 during advancement, during retraction, and during any diagnosis or therapy delivery associated with the treatment or diagnostic catheter.

For example, in FIG. 7A, radial seal 815 is employed to seal around a circumferential surface of dilator catheter 800. These radial seals are also required to seal the lumen shut during an exchange between the dilator catheter and another catheter, (e.g., after the catheter sheath is positioned in the body and before a second catheter is advanced through the catheter sheath). It is important to note that these radial seals may need to seal against both pressure gradients arising outwardly from the body as well as inwardly into the body. For example, in cardiac applications, the radial seals may need to seal against both pressure gradients arising outwardly from the vascular system outwards, as well as inwards into the vascular system, depending on the location of the distal end 812b of the catheter sheath 812 in the body, the time point in the cardiac cycle, the blood pressure, and the elevation of the proximal end 812a of the catheter sheath 812 above the distal end 812b.

These radial seals are typically required to be made of deflectable and deformable materials that can create a seal around a large variance in diameter and are therefore limited by how large they can grow. Having two radial seals in series, one optimized to seal around a small diameter and another optimized to seal around a larger diameter, is also known in the art, but this solution suffers from the problem of having air bubbles caught in between the two radial seals and not having sufficient control of the air to be certain that it does not advance into the body. Due to limitations of materials, the seals known in the art have limitations with respect to the largest diameters they can function on effectively, attempting to balance friction on the dilator catheter or additional catheter with sealing pressure in a state in which the lumen is empty of any catheter, balancing usability against patient safety.

There is, therefore, a need in the art for improved solutions for eliminating undesired fluid, such as air, from various catheters and from within the lumens of catheter sheaths.

SUMMARY

At least the above-discussed need is addressed and technical solutions are achieved by various embodiments of the present invention. According to various embodiments, a catheter sheath device may be summarized as including an elongate member, at least a portion thereof configured to be insertable into a body of a patient, the elongate member including a proximal end portion, a distal end portion, and a first lumen extending between the proximal end portion of the elongate member and the distal end portion of the elongate member, the first lumen sized to allow delivery of at least a distal end portion of a catheter therethrough. According to various embodiments, the catheter sheath device may include a moveable member physically coupled to the proximal end portion of the elongate member to permit relative movement therebetween, the moveable member including a second lumen extending through the moveable member, the second lumen sized to allow delivery of the at least the distal end portion of the catheter therethrough. According to various embodiments, the moveable member may be physically coupled to the proximal end portion of the elongate member to cause, via a first relative movement between the moveable member and the proximal end portion of the elongate member, the second lumen to be positioned at a first location relative to the proximal end portion of the elongate member that permits delivery of the at least the distal end portion of the catheter into the second lumen but not into the first lumen from the second lumen. According to various embodiments, the moveable member may be physically coupled to the proximal end portion of the elongate member to cause, via a second relative movement between the moveable member and the proximal end portion of the elongate member, the second lumen to be positioned at a second location relative to the proximal end portion of the elongate member that permits delivery of the at least the distal end portion of the catheter through both the second lumen and the first lumen.

In some embodiments, at least in a state in which the second lumen is positioned at the first location relative to the proximal end portion of the elongate member, no portion of the second lumen may overlap the first lumen as viewed along a viewing direction extending along a longitudinal axis of the second lumen toward the proximal end portion of the elongate member.

In some embodiments, the second lumen may extend from a first surface of the moveable member to a second surface of the moveable member, the first surface providing an internal surface of the catheter sheath device and the second surface providing an external surface of the catheter sheath device. In some embodiments, the second lumen may provide an entry port configured to permit entry of the at least the distal end portion of the catheter into the catheter sheath device prior to entry of the at least the distal end portion of the catheter into any other port provided by the catheter sheath device at least in a state in which the at least the distal end portion of the catheter is being delivered into the catheter sheath device.

In some embodiments, the catheter sheath device may be configured to permit the at least the distal end portion of the catheter to be receivable in the second lumen in a state in which the second lumen is positioned at the first location relative to the proximal end portion of the elongate member and in a state in which the second lumen is positioned at the second location relative to the proximal end portion of the elongate member. In some embodiments, the catheter sheath device may be configured, in a state in which the catheter is coupled to the catheter sheath device to permit entry of the at least the distal end portion of the catheter into the second lumen, to move the at least the distal end portion of the catheter between a first particular location in which the at least the distal end portion of the catheter is positioned to permit entry of the at least the distal end portion of the catheter into the first lumen, and a second particular location in which the at least the distal end portion of the catheter is positioned to prevent entry of the at least the distal end portion of the catheter into the first lumen.

In some embodiments, (a) the first relative movement between the moveable member and the proximal end portion of the elongate member, (b) the second relative movement between the moveable member and the proximal end portion of the elongate member, or each of (a) and (b) may occur transversely to a longitudinal axis of the second lumen. In some embodiments, (a) the first relative movement between the moveable member and the proximal end portion of the elongate member, (b) the second relative movement between the moveable member and the proximal end portion of the elongate member, or each of (a) and (b) may include a translational relative movement between the moveable member and the proximal end portion of the elongate member. In some embodiments, (a) the first relative movement between the moveable member and the proximal end portion of the elongate member, (b) the second relative movement between the moveable member and the proximal end portion of the elongate member, or each of (a) and (b) may include a rotational relative movement between the moveable member and the proximal end portion of the elongate member. In some embodiments, (a) the first relative movement between the moveable member and the proximal end portion of the elongate member, (b) the second relative movement between the moveable member and the proximal end portion of the elongate member, or each of (a) and (b) may include movement of the moveable member.

In some embodiments, the catheter sheath device may include a first sealing surface and a second sealing surface configured to seal against the first sealing surface to at least restrict fluid leakage between the first sealing surface and the second sealing surface at least (a) in a state in which the second lumen is positioned at the second location relative to the proximal end portion of the elongate member, (b) in a state in which the second lumen is positioned at the first location relative to the proximal end portion of the elongate member, or (a) and (b). In some embodiments, the first sealing surface may include a first opening arranged in fluidic communication with the first lumen, and the second sealing surface may include a second opening arranged in fluidic communication with the second lumen. In some embodiments, the first sealing surface may be provided by a first lubricous polymer layer backed by a first elastomeric layer, and the second sealing surface may be provided by a second lubricous polymer layer backed by a second elastomeric layer. In some embodiments, the first sealing surface, the second sealing surface, or each of the first sealing surface and the second sealing surface may be a planar sealing surface. In some embodiments, the catheter sheath device may include at least one mechanical spring configured to bias (a) the first sealing surface against the second sealing surface, or (b) the second sealing surface against the first sealing surface.

In some embodiments, the moveable member may include a third lumen extending through the moveable member, the third lumen spaced from the second lumen, and, at least in a state in which the second lumen is positioned at the first location relative to the proximal end portion of the elongate member, the third lumen may be positioned to be in fluidic communication with the first lumen. In some embodiments, at least in a state in which the second lumen is positioned at the second location relative to the proximal end portion of the elongate member, the third lumen may be fluidically disconnected from the first lumen. In some embodiments, at least in a state in which the second lumen is positioned at the second location relative to the proximal end portion of the elongate member, the moveable member may be configured to restrict transfer of fluid between the third lumen and the first lumen. In some embodiments, the second lumen and the third lumen may extend through the moveable member along parallel directions. In some embodiments, the third lumen may be sized to restrict delivery of the at least the distal end portion of the catheter through the third lumen.

In some embodiments, the proximal end portion of the elongate member may include a fourth lumen extending through the proximal end portion of the elongate member, the fourth lumen spaced from the first lumen, and, at least in the state in which the second lumen is positioned at the first location relative to the proximal end portion of the elongate member, the second lumen may be positioned to be in fluidic communication with the fourth lumen. In some embodiments, at least in a state in which the second lumen is positioned at the second location relative to the proximal end portion of the elongate member, the second lumen may be fluidically disconnected from the fourth lumen. In some embodiments, at least in a state in which the second lumen is positioned at the second location relative to the proximal end portion of the elongate member, and at least in the state in which the second lumen is positioned at the first location relative to the proximal end portion of the elongate member, the fourth lumen and the third lumen may be fluidically disconnected. In some embodiments, the fourth lumen may be sized to restrict delivery of the at least the distal end portion of the catheter through the fourth lumen. In some embodiments, the fourth lumen and the first lumen are fluidically disconnected.

In some embodiments, the catheter sheath device may further include an interlock mechanism configured to restrict relative movement between the moveable member and the proximal end portion of the elongate member in a state in which the second lumen is positioned at the first location relative to the proximal end portion of the elongate member.

According to some embodiments, various catheter sheath devices may include subsets or combinations of the elements and features described above.

Various embodiments of the present invention may include systems, devices, or machines that are or include combinations or subsets of any one or more of the systems, devices, or machines and associated features thereof described herein.

Further, all or part of any one or more of the systems, devices, or machines discussed herein or combinations or sub-combinations thereof may implement or execute all or part of any one or more of the processes or methods discussed herein or combinations or sub-combinations thereof.

According to some embodiments, a method of delivering at least a distal end portion of a catheter through at least a portion of a catheter sheath device including an elongate member, at least a portion of the elongate member configured to be insertable into a body of a patient is provided. The method may be summarized as including providing, in a first state in which a first relative positioning exists between (a) a first lumen within and extending from a proximal end portion of the elongate member of the catheter sheath device, and (b) a second lumen provided in a moveable member of the catheter sheath device, a first relative movement between the moveable member and the proximal end portion of the elongate member to establish a second relative positioning between the first lumen and the second lumen that permits the at least the distal end portion of the catheter to be delivered into the first lumen from the second lumen, the first relative positioning allowing delivery of the at least the distal end portion of the catheter into the second lumen, the first relative positioning restricting the at least the distal end portion of the catheter from being delivered into the first lumen from the second lumen, the moveable member physically coupled to the proximal end portion of the elongate member. In some embodiments, the method may include delivering the at least the distal end portion of the catheter into the first lumen from the second lumen at least in a second state in which the second relative positioning exists between the first lumen and the second lumen, the catheter sheath device configured to permit delivery of the at least the distal end portion of the catheter into the second lumen in each of the first state and the second state.

According to various embodiments, the first relative movement between the moveable member and the proximal end portion of the elongate member may reposition the at least the distal end portion of the catheter relative to the proximal end portion of the elongate member.

According to some embodiments, the moveable member may include a third lumen extending through the moveable member, the third lumen spaced from the second lumen, and, at least in the first state, the method may include delivering fluid between the first lumen and the third lumen. According to some embodiments, at least in the second state, the third lumen may be fluidically disconnected from the first lumen. According to some embodiments, the third lumen may be sized to restrict delivery of the at least the distal end portion of the catheter through the third lumen.

According to some embodiments, the proximal end portion of the elongate member may include a fourth lumen extending into the proximal end portion of the elongate member, the fourth lumen spaced from the first lumen, and, at least in the first state, the method may include delivering fluid into the fourth lumen from the second lumen. According to some embodiments, at least in the second state, the second lumen may be fluidly disconnected from the fourth lumen. According to some embodiments, the fourth lumen may be sized to restrict delivery of the at least the distal end portion of the catheter through the fourth lumen. According to some embodiments, the fourth lumen and the first lumen may be fluidically disconnected.

According to some embodiments, various methods may include subsets or combinations of the elements and actions of the methods described above.

According to some embodiments, a method of delivering at least part of a catheter into a first lumen of a catheter sheath device is provided. The first lumen is within and extends from a proximal end portion of an elongate member of the catheter sheath device, and at least a portion of the elongate member configured to be insertable into a body of a patient. The method may be summarized as including physically constraining the catheter with respect to the catheter sheath device in a first configuration of engagement with the catheter sheath device that provides the catheter no access to the first lumen. According to some embodiments, the method may include providing relative movement between a moveable member and the proximal end portion of the elongate member to reposition the physically constrained catheter into a second configuration of engagement with the catheter sheath device that provides the catheter access to the first lumen, the moveable member being physically coupled to the proximal end portion of the elongate member. According to various embodiments, the method may include delivering the at least part of the catheter into the first lumen in a state in which the catheter is in the second configuration of engagement.

According to various embodiments, the catheter sheath device may be configured to prevent relative movement between the moveable member and the proximal end portion of the elongate member in absence of the physically constraining the catheter with respect to the catheter sheath device in the first configuration of engagement.

According to various embodiments, the physically constraining the catheter with respect to the catheter sheath device in the first configuration of engagement with the catheter sheath device may include physically constraining relative movement between at least a distal end portion of the catheter and the moveable member to be predominantly along a first axis. In some embodiments, the first axis may be parallel to a longitudinal axis of the first lumen. In some embodiments, the first axis and the longitudinal axis of the first lumen may be colinear in a state in which the catheter is in the second configuration of engagement. In some embodiments, the moveable member includes a second lumen, and the first axis may be parallel to a longitudinal axis of the second lumen. In some embodiments, the delivering the at least part of the catheter into the first lumen in the state in which the catheter is in the second configuration of engagement may include delivering the at least part of the catheter into the first lumen from the second lumen. In some embodiments, the providing relative movement between the moveable member and the proximal end portion of the elongate member to reposition the physically constrained catheter into the second configuration of engagement with the catheter sheath device comprises causing the second lumen to overlap at least part of the first lumen as viewed along a viewing direction extending along the longitudinal axis of the second lumen. In some embodiments, the providing relative movement between the moveable member and the proximal end portion of the elongate member to reposition the physically constrained catheter into the second configuration of engagement with the catheter sheath device may include providing relative movement between the moveable member and the proximal end portion of the elongate member along a second axis that is not parallel with the first axis.

According to various embodiments, the physically constraining the catheter with respect to the catheter sheath device in the first configuration of engagement with the catheter sheath device may include restricting relative movement between at least a distal end portion of the catheter and the moveable member along a second axis. In some embodiments, the second axis may be perpendicular to a longitudinal axis of the first lumen.

According to some embodiments, the physically constraining the catheter with respect to the catheter sheath device in the first configuration of engagement with the catheter sheath device may include physically coupling a fluid-containing vessel to the catheter sheath device, at least a portion of the catheter physically constrained to move within the fluid-containing vessel. According to some embodiments, the physically constraining the catheter with respect to the catheter sheath device in the first configuration of engagement with the catheter sheath device may include physically coupling a fluid-containing vessel to the moveable member, at least a portion of the catheter physically constrained to move within the fluid-containing vessel.

According to some embodiments, various methods may include subsets or combinations of the elements and actions of the methods described above.

According to some embodiments, a method of providing a vessel with access to a first lumen of a catheter sheath device is provided. The first lumen may be within and extends from a proximal end portion of an elongate member of the catheter sheath device, and at least a portion of the elongate member configured to be insertable into a body of a patient. According to various embodiments, the method may be summarized as including providing the vessel in a first state in which the vessel is physically coupled to the catheter sheath device at a first location relative to the proximal end portion of the elongate member, and in which at least a portion of a catheter is located in an internal cavity of the vessel, the physically coupled vessel at the first location providing the portion of the catheter in the internal cavity of the vessel no access to the first lumen. In some embodiments, the method may include providing relative movement between a moveable member and the proximal end portion of the elongate member to position the physically coupled vessel at a second location relative to the proximal end portion of the elongate member, the second location other than the first location, the physically coupled vessel at the second location providing the portion of the catheter in the internal cavity of the vessel access to the first lumen, the moveable member physically coupled to the proximal end portion of the elongate member.

According to various embodiments, the vessel may contain fluid in the internal cavity of the vessel. In some embodiments, the internal cavity of the physically coupled vessel at the first location may be fluidically disconnected from the first lumen, and the internal cavity of the physically coupled vessel at the second location may be fluidically connected to the first lumen.

According to some embodiments, the method may include conveying fluid between a fluid supply and the first lumen in the first state. In some embodiments, the conveying the fluid between the fluid supply and the first lumen may include conveying the fluid through a particular lumen provided in the moveable member, the particular lumen fluidically disconnected from the internal cavity of the vessel. In some embodiments, the fluid supply may be fluidically disconnected from the internal cavity of the vessel during the conveying the fluid between the fluid supply and the first lumen.

According to some embodiments, the catheter sheath device may be configured to prevent relative movement between the moveable member and the proximal end portion of the elongate member in absence of a physical coupling of the vessel to the catheter sheath device.

According to some embodiments, the catheter sheath device may be configured to allow the vessel to be decouplable from the catheter sheath device at least at the first location, and the catheter sheath device may be configured to physically restrict the physically coupled vessel from being decoupled from the catheter sheath device at the second location.

According to some embodiments, the portion of the catheter is a distal end portion of the catheter, and the method may include delivering the catheter distal-end-portion-first into the first lumen in a state in which the physically coupled vessel is at the second location.

According to some embodiments, in the first state, at least the portion of the catheter may be located in the internal cavity of the vessel. In some embodiments, in the first state, fluid may be located in the internal cavity of the vessel.

According to various embodiments, the method may include delivering the portion of the catheter into the first lumen from the internal cavity of the physically coupled vessel located at the second location. In some embodiments, the portion of the catheter is a distal end portion of the catheter. In some embodiments, the distal end portion of the catheter may be selectively configurable between a delivery configuration in which the distal end portion of the catheter is sized to be deliverable through the first lumen and a deployed configuration in which the distal end portion of the catheter is sized too large to be deliverable through the first lumen. In some embodiments, the delivering the portion of the catheter into the first lumen from the internal cavity of the physically coupled vessel located at the second location may include delivering the distal end portion of the catheter in the delivery configuration into the first lumen from the internal cavity of the physically coupled vessel located at the second location.

According to various embodiments, the portion of the catheter is a distal end portion of the catheter. In some embodiments, the distal end portion of the catheter may be selectively configurable between a delivery configuration in which the distal end portion of the catheter is sized to be deliverable through the first lumen and a deployed configuration in which the distal end portion of the catheter is sized too large to be deliverable through the first lumen. In some embodiments, at least the distal end portion of the catheter may be provided in the delivery configuration in the internal cavity of the vessel.

According to various embodiments, the portion of the catheter is a distal end portion of the catheter. In some embodiments, the distal end portion of the catheter may be selectively configurable between a delivery configuration in which the distal end portion of the catheter is sized to be deliverable through the first lumen and a deployed configuration in which the distal end portion of the catheter is sized too large to be deliverable through the first lumen. In some embodiments, the internal cavity of the vessel may be insufficiently sized to permit the distal end portion of the catheter to be provided therein in the deployed configuration.

According to some embodiments, various methods may include subsets or combinations of the elements and actions of the methods described above.

It should be noted various embodiments of the present invention include variations of the methods described or shown in the figures and, accordingly, are not limited to the actions described or shown in the figures or their ordering, and not all actions shown or described are required according to various embodiments. According to various embodiments, such methods may include more or fewer actions and different orderings of actions. Any of the features of all or part of any one or more of the methods or processes discussed herein may be combined with any of the other features of all or part of any one or more of the methods and processes discussed herein.

Any of all or part of one or more of the methods or processes and associated features thereof discussed herein may be implemented or executed by all or part of a device system, apparatus, or machine, such as all or a part of any of one or more of the systems, apparatuses, or machines described herein or a combination or sub-combination thereof.

BRIEF DESCRIPTION OF THE DRAWINGS

It is to be understood that the attached drawings are for purposes of illustrating aspects of various embodiments and may include elements that are not to scale.

FIGS. 1C and 1D illustrate a sequence of movement of a moveable member of a catheter sheath device, according to some embodiments of the present invention.

FIGS. 2A-2E illustrate various embodiments of a moveable member of a catheter sheath device.

DETAILED DESCRIPTION

Figure 1A:
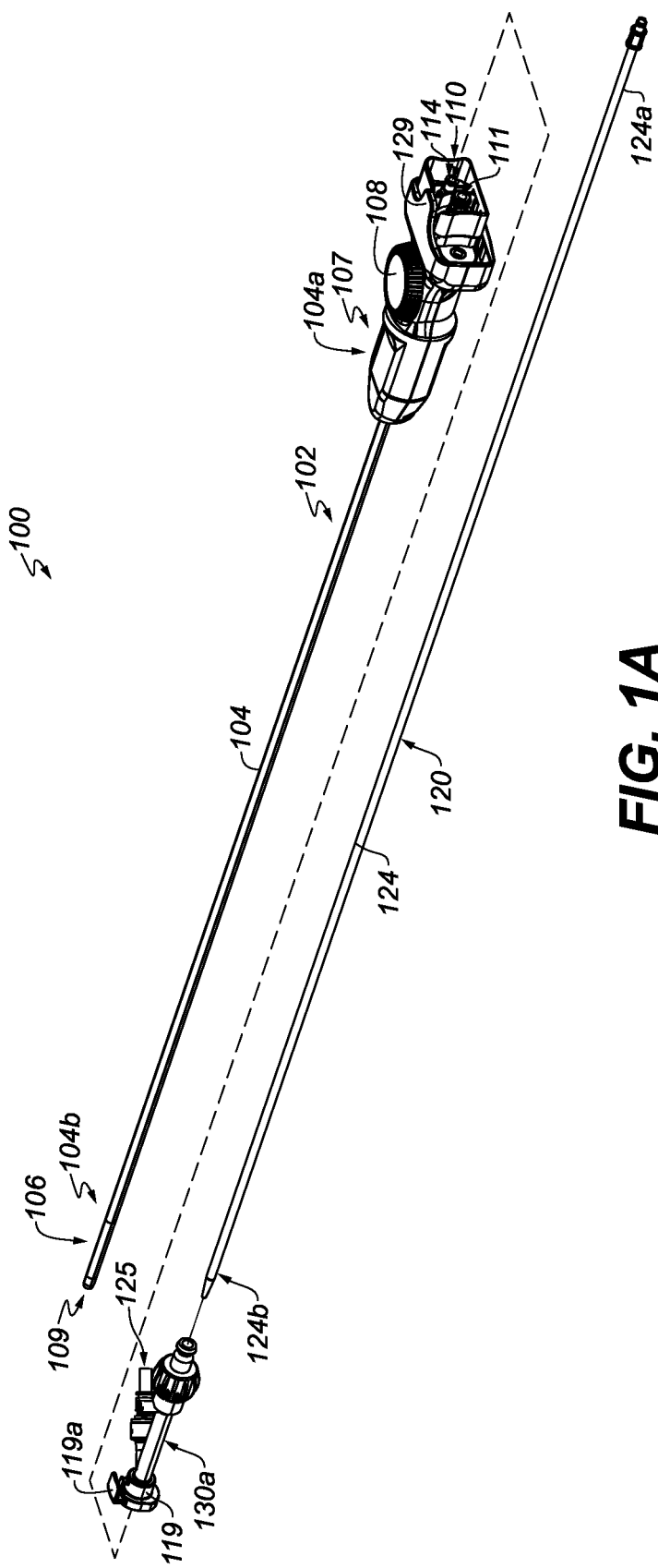
FIG. 1A illustrates a catheter device system including a catheter sheath device and a catheter, according to some embodiments of the present invention.

Various embodiments of the present invention address the above-discussed need and provide technical solutions in the art with inventive catheter sheath devices and methods of operating one or more catheter sheath devices according to various embodiments. In some embodiments, a moveable member of a catheter sheath device may be physically coupled to a proximal end portion of an elongate member of the catheter sheath device, where at least a portion of the elongate member may be configured to be insertable into a body of a patient. For example, the elongate member may be a catheter sheath. In this regard, in some embodiments, the elongate member includes a first lumen that extends through the elongate member, and the elongate member may be configured to facilitate delivery of a catheter through the first lumen to a bodily cavity within a patient.

In some embodiments, the moveable member forms at least part of a sliding mechanism that, when moved, changes a fluidic connection configuration or state between various lumens. In some embodiments, the moveable member may be configured to, in a first connection configuration or state, fluidically connect the first lumen of the elongate member on an output side of the moveable member to a third lumen coupled to a lumen on an input side of the moveable member, and to fluidically connect a fourth lumen on the output side of the moveable member to a second lumen coupled to a lumen, such as an internal cavity of a vessel, on the input side of the moveable member. The second lumen coupled to the internal cavity of the vessel on the input side, may be configured to contain within it at least a portion of a catheter configured to be inserted into a bodily cavity of a patient in order to perform one or more operations on or within the bodily cavity or otherwise on or within the patient.

The first connection configuration or state may be a flushing configuration or state, where (a) flushing fluid may be provided from the third lumen coupled to, e.g., a fluid source on the input side, into the first lumen of the elongate member to flush the elongate member of undesired fluid such as air (e.g., prior to insertion into a body of a patient), and (b) flushing fluid may be provided into the second lumen via e.g., a flushing port coupled to the internal cavity of the vessel on the input side, where flushing fluid that flushes the internal cavity of the catheter vessel may be discharged through the fourth lumen on the output side, in order to flush the undesired fluid such as air (e.g., prior to insertion of the catheter into the elongate member of the catheter sheath device).

The moveable member may include or interact with one or more sealing surfaces and mechanical springs that restrict fluid leakage throughout a sliding movement of the moveable member from the first connection configuration or state to a second connection configuration or state. In some embodiments, the second connection configuration or state may be an operative connection configuration or state, where the second lumen coupled to the internal cavity of the catheter vessel on the input side, becomes fluidically connected to the first lumen of the elongate member, so that the catheter may, e.g., be delivered through the first lumen to a bodily cavity of a patient for operation.

According to some embodiments, by allowing flushing of the first lumen of the elongate member of the catheter sheath device and the second lumen coupled to the catheter-containing vessel in the first flushing connection configuration or state, where the first lumen and the second lumen are fluidically disconnected, entry of undesired fluid (e.g., air) into the first lumen from the second lumen and vice versa by the respective flushing operations may be prevented or lessened. Then, according to some embodiments, in a state in which the respective flushing operations are completed, the moveable member may be configured to safely fluidically connect the first lumen and the second lumen, so that a catheter in the vessel can be delivered from the second lumen into the first lumen of the elongate member of the catheter sheath device for delivery into a body of a patient in cases where an operation on the patient is being performed. In addition, the first flushing connection configuration or state allows catheters to be switched or exchanged in a state in which the catheter vessel is fluidically disconnected from the first lumen of the elongate member of the catheter sheath device, thereby preventing or at least reducing the risk of introduction of undesired fluid into the first lumen of the elongate member during the switching or exchanging of the catheter. For at least these reasons, various embodiments provide, for example, improved catheter-to-catheter-sheath flushing, sealing, and interactions and reduce the risk of introduction of undesired fluid into the catheter and catheter sheath.

Of course, the above-discussed and other flushing procedures and configurations of the moveable member according to various embodiments may be performed in other cases besides those involving operation on a patient including, e.g., at least when manufacturing, testing, performing quality control, or training on a moveable member according to various embodiment, or on one or more other components of the catheter sheath device, according to various embodiments.

It should be noted that the above discussion and the other disclosures herein are not intended to be limiting and merely are provided for illustrating some of the various aspects of some of the various embodiments of the present invention. In this regard, for example, although the above examples are discussed in terms of particular numbers of lumens couplable on the input side of the moveable member and particular numbers of lumens on the output side of the moveable member, one or more lumens may be provided for each of the input side and the output side. For another example, although the above examples are discussed in terms of two fluidic connection configurations or states, two or more connection configurations or states may be provided according to various embodiments. For yet another example, merely for illustration purposes, some embodiments do not include the above-discussed fourth lumen on the output side of the moveable member, and, in at least some of those embodiments, flushing-fluid discharge for, e.g., the above-discussed second lumen may occur at another location, e.g., from a location within the catheter vessel. These and other changes can be made to various embodiments of the invention in light of the descriptions herein and still fall within the scope of the present invention.

In this regard, in the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'based at least on A' includes A as well as the possibility of one or more other additional elements besides A. In the same manner, the phrase, 'based on A' includes A, as well as the possibility of one or more other additional elements besides A. However, the phrase, 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", and the phrase "device system" all are intended to include one or more physical devices or sub-devices (e.g., pieces of equipment) that interact to perform one or more functions. The word "device" may equivalently be referred to as a "device system" in some embodiments.

Further, the phrase "in response to" may be used in this disclosure. For example, this phrase may be used in the following context, where an event A occurs in response to the occurrence of an event B. In this regard, such phrase includes, for example, that at least the occurrence of the event B causes or triggers the event A.

In some embodiments, the term "adjacent", the term "proximate", and the like refer at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", and the like additionally or alternatively refers to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", and the like additionally or alternatively refers to at least a sufficient closeness between the objects defined as adjacent, proximate, and the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", and the like are not limited to any of the above example definitions, according to some embodiments. In addition, the term "adjacent" and the term "proximate" do not have the same definition, according to some embodiments.

The term "proximal", in the context of a proximal portion, proximal location, and the like of a medical device, includes, for example, the portion, location, and the like, being or being configured to be further away from a patient or portion of or region within a patient (e.g., a bodily cavity) intended to be treated or assessed by the medical device, as compared to a distal portion, location, and the like of the medical device, according to some embodiments. In some embodiments, the term "proximal", in the context of a proximal portion, proximal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, after or behind a distal portion, location, and the like of the medical device. On the other hand, the term "distal", in the context of a distal portion, distal location, and the like of a medical device, includes, for example, the portion, location, and the like, being or being configured to be closer to a patient or portion of or region within a patient (e.g., a bodily cavity) intended to be treated or assessed by the medical device, as compared to a proximal portion, location, and the like of the medical device, according to some embodiments. In some embodiments, the term "distal", in the context of a distal portion, distal location, and the like of a medical device, includes, for example, the portion, location, and the like, being or being configured to be delivered (e.g., percutaneously or intravascularly) toward a patient or portion of or region within a patient (e.g., a bodily cavity) intended to be treated or assessed by the medical device, before or ahead of a proximal portion, location, and the like of the medical device.

The word "ablation" may be used in this disclosure and should be understood to include, for example, any disruption to certain properties of bodily tissue. Most commonly, the disruption is to the electrical conductivity and is achieved by heating, which can be generated with resistive or radio-frequency (RF) techniques for example. However, any other technique for such disruption may be included when the term "ablation" is used, such as mechanical, chemical, electroporation or optical techniques Various catheters described in this disclosure, may in some embodiments, be employed to deliver ablative energy.

The phrase "bodily opening" as used in this disclosure should be understood to include, for example, a naturally occurring bodily opening or channel or lumen; a bodily opening or channel or lumen or perforation formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath or catheter introducer) may be present in various embodiments. These elements may provide a passageway through a bodily opening for various devices employed in various embodiments.

The phrase "bodily cavity" as used in this disclosure should be understood to mean a cavity in a body. The bodily cavity may be a cavity provided in a bodily organ (e.g., an intra-cardiac cavity or chamber of a heart). The bodily cavity may be provided by a bodily vessel.

The word "tissue" as used in some embodiments in this disclosure should be understood to include, for example, any surface-forming tissue that is used to form a surface of a body or a surface within a bodily cavity, a surface of an anatomical feature or a surface of a feature associated with a bodily opening positioned in fluidic communication with the bodily cavity. The tissue can include, for example, part or all of a tissue wall or membrane that defines a surface of the bodily cavity. In this regard, the tissue can form an interior surface of the cavity that surrounds a fluid within the cavity. In the case of cardiac applications, tissue can include, for example, tissue used to form an interior surface of an intra-cardiac cavity such as a left atrium or right atrium. In some embodiments, tissue is non-excised tissue. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include, for example, an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed.

The phrase "physically coupled" is intended to include, in some embodiments, a coupling between two objects that involves a coupling between the two objects that may restrict some form of movement (e.g., translation or rotation or both translation and rotation) therebetween. In some embodiments, the two objects physically contact each other at least in one state of the physical coupling between the two objects. In some embodiments, the two objects do not directly physically contact each other at least in one state of the physical coupling between the two objects (e.g., a coupler or other coupling member positioned between the two objects to couple them together). The phrase "physically coupled" is intended to include, in some embodiments, a coupling between two objects that involves one or more other objects arranged to couple the two objects together to achieve a desired interaction between the two objects. The phrases, "moveably coupled", "moveable coupling", and the like are intended to include, in some embodiments, a physical coupling between two objects that at least allows relative movement between the two objects. The phrase "rotationally coupled" and the like is intended to include, in some embodiments, a coupling between two objects that at least allows relative rotational movement between the two objects. For example, one of the two objects may be rotationally coupled to the other of the two objects via a rotational bearing or guide. The phrases "translationally coupled", "slidably coupled", "slideable coupling", and the like are intended to include, in some embodiments, a coupling between two objects that at least allows relative sliding or translational movement along a particular path. In some embodiments, a translational or slidable coupling allows translation along a particular axis while restricting or preventing relative movement between the two objects along a second axis. In some embodiments, a translational or slidable coupling is provided by various guide surfaces arranged to guide the translational movement. The phrases "fixedly coupled", "permanently coupled", and the like, are intended to include, in some embodiments, a secure coupling between two objects that, in some embodiments, does not involve or include a mechanism configured to release the coupling of the two objects. The phrases "removably coupled", "detachably coupled", and the like, are intended to include, in some embodiments, a coupling between two objects that, in some embodiments, allows such coupling to be repeatedly disengaged and re-engaged without damaging the coupling (if a distinct coupling mechanism exists, e.g., in contrast to an interference fit that relies on friction), without damaging either or both of the objects, or without damaging the coupling (if a distinct coupling mechanism exists) and without damaging either or both of the objects. The phrase "operatively coupled" is intended to include, for example, a coupling between two objects that transmits force, energy, information, or other influence at least from one of the two objects to the other of the two objects. An operative coupling does not exclude the possibility of a physical or fixed coupling in addition to the operative coupling. Unless otherwise explicitly noted or required by context, for any connection or coupling, direct or indirect, between components, devices, or other physical objects described herein, different embodiments include different ones of the above-described coupling types for such components, devices, or other physical objects. For example, unless otherwise explicitly noted or required by context, if a first physical object is shown in the figures or described in this text as being connected or coupled, directly or indirectly, to a second physical object; some embodiments will have the first physical object fixedly coupled to the second physical object; other embodiments will have the first physical object moveably coupled to the second physical object; other embodiments will have the first physical object rotationally coupled to the second physical object; other embodiments will have the first physical object translationally coupled to the second physical object; other embodiments will have the first physical object slidably coupled to the second physical object; other embodiments will have the first physical object permanently coupled to the second physical object; other embodiments will have the first physical object removably or detachably coupled to the second physical object; other embodiments will have the first physical object not fixedly or permanently coupled to the second physical object while having the first physical object physically coupled to the second physical object; other embodiments will have the first physical object not physically coupled or fixedly coupled to the second physical object, but will have the first physical object operatively coupled to the second physical object; etc.

The word "fluid", as used in this disclosure, should be understood to include, for example, liquid, or gas. In this regard, various embodiments of the present invention are described herein in the context of providing a flushing fluid to flush a medical device of undesired fluid (e.g., air). While it is quite common for the flushing fluid to be a liquid, such as saline, which is used to flush, e.g., undesired air from a medical device prior to insertion of the medical device into the body of a patient, the present inventors contemplate that there may be certain types of desirable gas that may be used to flush undesirable fluid, such as air, from a medical device. For example, the present inventors contemplate that carbon dioxide might be an option as a desirable flushing gas to flush undesired fluid (e.g., air) from a medical device. Accordingly, the present specification retains the usage of the phrase "flushing fluid" and the like with the thought that gas might be able to be used as a flushing fluid, even though many common implementations likely will utilize a flushing liquid, such as saline.

In some embodiments, the phrases "fluidic communication", "fluidic connection", "fluidically communicate", "fluidically coupled", "fluidly communicate", "fluidly coupled", and the like, are intended to include, for example, a port or opening, of a physical object leading to a lumen or other internal cavity, where the port, opening, lumen, or internal cavity leads to a body (e.g., a source or drain) of a first fluid, such that (a) at least some of the first fluid moves or is able to move through (1) the port or opening into the lumen or other internal cavity, (2) the lumen or other internal cavity into the port or opening, or both (a)(1) and (a)(2); (b) at least some of a second fluid moves or is able to move through (1) the lumen or other internal cavity into the port or opening, (2) the port or opening into the lumen or other internal cavity, or both (b)(1) and (b)(2); or both (a) and (b). In some embodiments, the first fluid and the second fluid are the same. In some embodiments, the first fluid and the second fluid are different.

Various embodiments of catheter device systems and catheter sheath devices are described herein. It should be noted that any catheter device system or catheter sheath device described herein may also be referred to as a medical system or medical device system. Some of the described devices of such systems and devices are medical devices that are percutaneously or intravascularly deployed. Some of the described devices are deployed through a bodily opening that is accessible without puncturing, cutting or otherwise perforating bodily tissue to create an access to the bodily opening. Some of the described devices employ transducer-based devices or device systems. Some of the described devices are moveable between a delivery or unexpanded configuration in which a portion of the device is sized, shaped, or both to be deliverable through a bodily opening leading to a bodily cavity, and an expanded or deployed configuration in which the portion of the device has a size, shape, or both too large to be deliverable through the bodily opening leading to the bodily cavity. The expanded or deployed configuration may be a configuration in which the device is in its operational or intended operational state in which the device is configured to operate or perform therapy on or within the bodily cavity.

FIG. 1A includes a catheter device system 100 including a catheter sheath device 102 and a catheter 120, according to some embodiments. According to various embodiments, the catheter sheath device 102 includes an elongate member 104 including a proximal end portion 104a and a distal end portion 104b. According to various embodiments, at least a portion of the elongate member 104 may be configured (e.g., sized and shaped) to be insertable or deliverable into a body of a patient or living being. For example, at least a portion of the elongate member 104 may be sized to be deliverable (e.g., percutaneously or intravascularly) into a patient's body via a bodily opening provided in the patient's body. According to some embodiments, the elongate member 104 may be arranged, or configured, to be insertable or deliverable distal end portion 104b—first into the patient's body. In some embodiments, at least some portion of the elongate member 104 (e.g., at least distal end portion 104b) may be configured to be insertable or deliverable into a patient's body, while other portions of the elongate member 104 may not. For example, in some embodiments, the proximal end portion 104a of the elongate member may be inappropriately shaped or inappropriately sized (e.g., too large) to be insertable or deliverable into a particular bodily opening that another portion of the elongate member 104 (e.g., at least distal end portion 104b) is configured to be insertable or deliverable therethrough. In some embodiments, the catheter sheath device 102 may include a housing 107 that encloses various actuators. For example, in some embodiments, one or more actuators may be employed to selectively bend or steer a portion of the catheter device system 100 (e.g., bendable portion 106 of elongate member 104), such as that shown, e.g., by International Publication No. WO2017/100902, which published on Jun. 22, 2017. It is noted that the ability to bend or steer a particular portion of the catheter device system 100 may, in some embodiments, facilitate insertion of at least a portion of the catheter device system 100 (e.g., at least a portion of the elongate member 104) into a patient's body, or delivery of at least a portion of the catheter device system 100 (e.g., at least a portion of the elongate member 104) to a particular desired destination in the patient's body. In some embodiments, the one or more actuators may be manually controlled by a user (e.g., a health care provider) (e.g., via control input 108). In some embodiments, the one or more actuators may be controlled as under the influence of an electrical energy supply system (e.g., as part of motorized system or a robotic system). In some embodiments, housing 107 may house electronic-based device systems. In some embodiments, housing 107 may house data processor-based device systems. In some embodiments, housing 107 may house computer-memory-based device systems. In some embodiments, housing 107 may be configured to function as a handle to allow gripping of the catheter sheath device 102 by a user at an intended location (e.g., a handle location on the catheter sheath device 102 intended to be gripped to promote manual manipulation of at least part of the catheter sheath device 102). In some embodiments, the housing 107 may be considered to be all or part of the proximal end portion 104a of the elongate member 104.

Figure 1B:
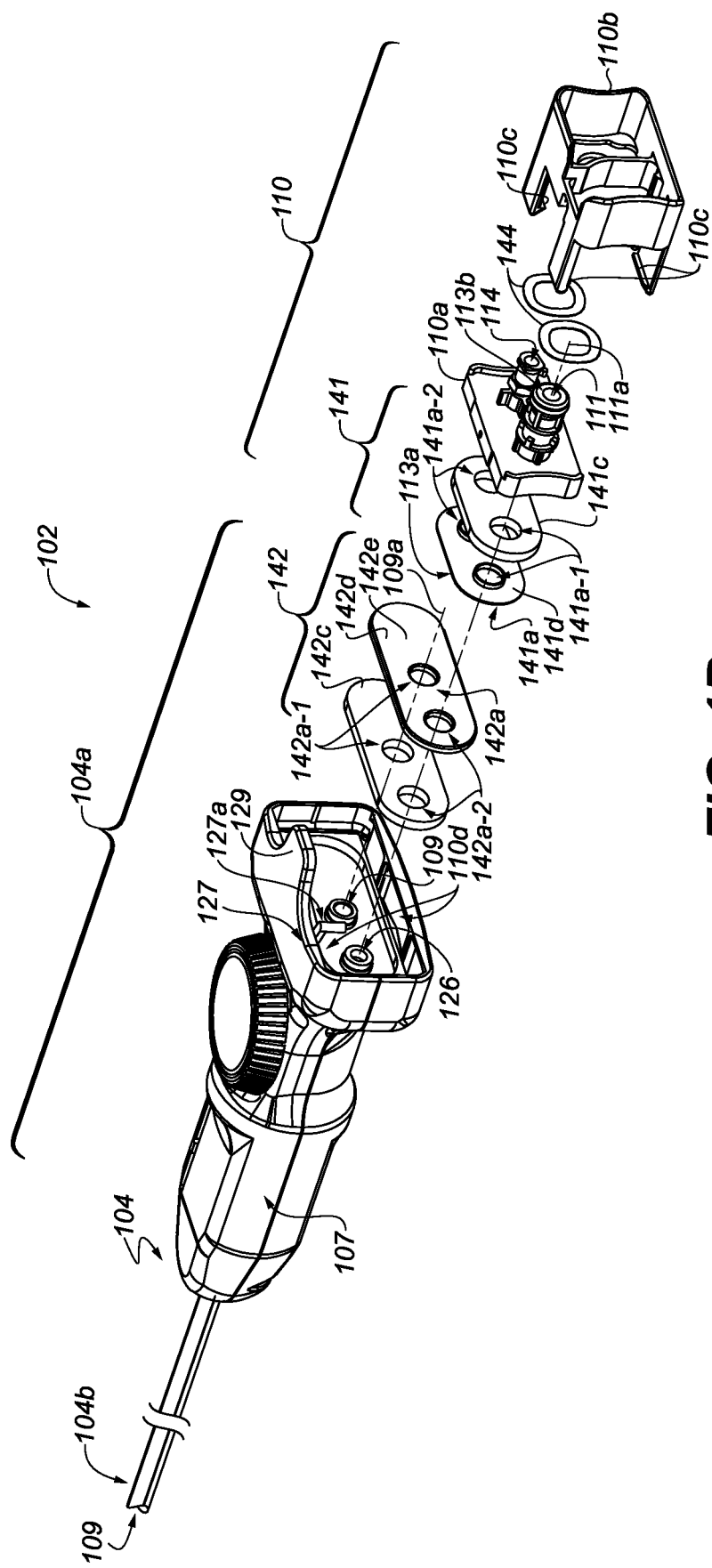
FIG. 1B illustrates an exploded view of a catheter sheath device, according to some embodiments of the present invention.

According to various embodiments, the elongate member 104 includes a first lumen 109 (see, e.g., the exploded view of the catheter sheath device 102 in FIG. 1B) extending between the proximal end portion 104a of the elongate member 104 and the distal end portion 104b of the elongate member 104. According to various embodiments, the first lumen 109 may extend from proximal end portion 104a of the elongate member 104 to the distal end portion 104b of the elongate member 104. According to various embodiments, the first lumen 109 may be located within the proximal end portion 104a of the elongate member 104 and may extend (e.g., distally) from the proximal end portion 104a of the elongate member 104. According to various embodiments, the first lumen 109 may be sized to allow delivery of at least a portion of a catheter (e.g., at least distal end portion 124b of catheter 120 in FIG. 1A) therethrough. In some embodiments, the distal end portion 124b of the catheter 120 may be selectively configurable between a delivery configuration in which the distal end portion 124b of the catheter 120 is sized to be deliverable through the first lumen 109 and a deployed configuration in which the distal end portion 124b of the catheter 120 is sized too large to be deliverable through the first lumen 109. According to various embodiments, the first lumen 109 may provide a passageway for a catheter (e.g., catheter 120). According to various embodiments where, e.g., the elongate member 104 may be a catheter sheath, at least a portion of the elongate member 104 of the catheter sheath device 102 may be insertable into a patient's body to shield the body from potential damage that may be caused by the delivery of a catheter (e.g., catheter 120) provided into the lumen (e.g., first lumen 109) of the catheter sheath.

According to various embodiments, catheter 120 includes an elongate member 124 that includes a distal end portion 124b and a proximal end portion 124a. According to various embodiments, the catheter may be advanced through the first lumen 109 from the proximal end portion 104a of the elongate member 104 toward the distal end portion 104b of the elongate member 104. According to various embodiments, the catheter may be advanced through the first lumen 109 from the proximal end portion 104a of the elongate member 104 toward the distal end portion 104b of the elongate member 104 until at least part of the catheter 120 protrudes outwardly from the distal end portion 104b of the elongate member 104. According to various embodiments, the catheter may be advanced distal end portion 124b first through the first lumen 109 from the proximal end portion 104a of the elongate member 104 toward the distal end portion 104b of the elongate member 104.

Different types of catheters (e.g., catheter 120) may be employed according to various embodiments. For example, according to some embodiments the catheter 120 can be an introducer or a dilator (e.g., a dilator catheter). In the form of a dilator catheter, catheter 120 may be inserted through the first lumen 109 of the elongate member 104 (e.g., from the proximal end portion 104a of elongate member 104 to the distal end portion 104b of the elongate member 104). In some embodiments, the dilator catheter, which may be catheter 120, could be pre-loaded into the first lumen 109, e.g., by being inserted into the first lumen 109 of the elongate member 104 prior to an insertion of any part of the catheter sheath device 102 into a patient's body. Upon completion of such an insertion through the first lumen 109, a tapered or point-like end of distal end portion 124b of such a dilator catheter 120 may protrude outwardly from the distal end portion 104b of the catheter sheath device 102. According to some embodiments, the catheter 120 and catheter sheath device 102 assembly may then be advanced through a bodily opening within the patient's body with the tapered or protruding point-like distal end of the distal end portion 124b of catheter 120 dilating or enlarging various parts of the bodily opening to facilitate the advancement of the assembly through the bodily opening. In some embodiments, the catheter 120 and catheter sheath device 102 assembly may be advanced over a previously deployed guidewire. Once the assembly has been successfully delivered through the bodily opening to a desired location within the body, the catheter 120 (and the guide wire, if employed) may be pulled out of the catheter sheath device 102 leaving at least the distal end portion 104b of the elongate member 104 of the catheter sheath device 102 behind in the bodily opening according to some embodiments. Catheter 120 may be exchanged with a second catheter in the first lumen 109 according to various embodiments. For example, after a dilator catheter is used to place at least part of the distal end portion 104b of the elongate member 104 of the catheter sheath device 102 in a proper location within a body of a patient, the dilator catheter may be removed and exchanged with a diagnostic or therapy-delivering catheter, which is then provided to the proper location within the body of the patient via the first lumen 109 of the elongate member 104. However, such a catheter exchange need not occur only in a state in which at least part of the distal end portion 104b of the elongate member 104 of the catheter sheath device 102 remains within the patient's body. In view of the above discussion, it can be seen that catheters (e.g., a diagnostic or therapy-delivering catheter) other than dilator catheters may be inserted into the first lumen 109 of the elongate member 104 of the catheter sheath device 102 according to various method embodiments of the present invention.

According to various embodiments, a moveable member 110 may be physically coupled to the proximal end portion 104a of the elongate member 104 of the catheter sheath device 102 to permit relative movement therebetween. In some embodiments, the physical coupling of the moveable member 110 to the proximal end portion 104a of the elongate member 104 may be a moveable coupling or slideable coupling to the proximal end portion 104a of the elongate member 104 of the catheter sheath device 102. In some embodiments, the moveable member 110 may be physically coupled to the housing 107 to permit relative movement therebetween. The housing 107 may, in some embodiments, be considered at least part of the proximal end portion 104a of the elongate member 104 of the catheter sheath device 102. According to various embodiments, moveable member 110 includes a second lumen 111 extending through the moveable member 110. In some embodiments, the second lumen 111 may extend from a first surface (e.g., first surface 113a, FIG. 1B) of the moveable member 110 to a second surface (e.g., second surface 113b, FIG. 1B of the moveable member 110, the first surface (e.g., first surface 113a) providing an internal surface of the catheter sheath device 102 and the second surface (e.g., second surface 113b) providing an external surface of the catheter sheath device 102. According to various embodiments, the second lumen 111 may be sized to allow delivery of at least a portion of the catheter 120 (e.g., at least distal end portion 124b) therethrough.

As shown, e.g., by viewing a sequence of FIG. 1D followed by FIG. 1C, the moveable member 110 may be physically coupled to the proximal end portion 104a of the elongate member 104 to cause, via a first relative movement between the moveable member 110 and the proximal end portion 104a of the elongate member 104, the second lumen 111 to be positioned at a first location 112a relative to the proximal end portion 104a of the elongate member 104, according to some embodiments. As shown, e.g., by viewing a sequence of FIG. 1C followed by FIG. 1D, the moveable member 110 may also be physically coupled to the proximal end portion 104a of the elongate member 104 to cause, via a second relative movement between the moveable member 110 and the proximal end portion 104a of the elongate member 104, the second lumen 111 to be positioned at a second location 112b relative to the proximal end portion 104a of the elongate member 104, according to some embodiments. The first relative movement, the second relative movement, or each of the first relative movement and the second relative movement may be or include a translational relative movement between the moveable member 110 and the proximal end portion 104a of the elongate member 104. For example, a comparison of FIGS. 1C and 1D shows a particular form of translational relative movement along an axis parallel to axis X-X that may exist between the moveable member 110 and proximal end portion 104a of the elongate member 104. The relative movements between the moveable member 110 and the proximal end portion 104a of the elongate member 104 (e.g., the above-discussed first and second relative movements) may include (i) movement of the moveable member 110, (ii) movement of the proximal end portion 104a of the elongate member 104, or both of (i) and (ii) according to various embodiments.

In some embodiments, the positioning of the moveable member 110 at the first location 112a relative to the proximal end portion 104a of the elongate member 104 may be considered a first configuration or state (such as that shown at least in FIG. 1C) that permits separate and possibly contemporaneous or concurrent flushing of (a) a vessel containing a catheter (e.g., vessel 118 containing catheter 120) fluidically coupled to the second lumen 111 and (b) the first lumen 109 of the elongate member 104 of the catheter sheath device 102, such that fluid exchange between first lumen 109 and the second lumen 111 does not occur. Accordingly, in some embodiments, for example, the positioning of the moveable member 110 at the first location 112a relative to the proximal end portion 104a of the elongate member 104 permits delivery of at least a portion of the catheter 120 (e.g., at least the distal end portion 124b), via, e.g., vessel 118, into the second lumen 111, but not into the first lumen 109 from the second lumen 111. Such a circumstance arises, for example, in a state in which the second lumen 111 and the first lumen 109 are fluidically disconnected, such as some embodiments according to the first configuration or state of at least FIG. 1C. For another example, in FIG. 1C, relative movement (e.g., translational relative movement along an axis parallel to the X-X axis) between the moveable member 110 and the proximal end portion 104a of the elongate member 104 has positioned the second lumen 111 at the first location 112a such that a longitudinal axis 111a of the second lumen 111 may be spaced apart from a longitudinal axis 109a of the first lumen 109 by an amount sufficient to restrict, preclude, or prevent entry of the at least the portion of the catheter 120 (e.g., at least the distal end portion 124b) into the first lumen 109 from the second lumen 111. In some embodiments, at least in a state in which the second lumen 111 is positioned at the first location 112a relative to the proximal end portion 104a of the elongate member 104, no portion of the second lumen 111 overlaps the first lumen 109 as viewed along a viewing direction extending along the longitudinal axis 111a of the second lumen 111 toward the proximal end portion 104a of the elongate member 104. For example, in some embodiments according to at least FIG. 1C, peering distally into the second lumen 111 down the longitudinal axis 111a would present the viewer with a view into fourth lumen 126 (shown, e.g., at least in FIG. 1D), but, due to the spacing of the longitudinal axis 111a from the axis 109a of the first lumen 109 in the state of at least FIG. 1C, the viewer would not see any part of the first lumen 109. In some embodiments, the second lumen 111 may be positioned at the first location 112a such that the at least the portion of the catheter 120 would not be impeded from being delivered into the second lumen 111. In some embodiments, no portion of the catheter sheath device 102 obstructs or prevents delivery of the at least the portion of the catheter 120 (e.g., at least the distal end portion 124b) into the second lumen 111 in the first location 112a.

It is noted that the term "longitudinal axis" as used in this disclosure may pertain to a member that is flexible in nature (e.g., an elongate member of a catheter sheath device or an elongate member of a catheter). Accordingly, it is understood that the longitudinal axis of such a member may, in some embodiments or states, assume a bent shape to reflect a bend in the corresponding member. On the other hand, of course, if such a member is at least in part straight, the corresponding region(s) of the longitudinal axis would also be straight and not have a bend.

According to some embodiments, the positioning of the moveable member 110 at the second location 112b relative to the proximal end portion 104a of the elongate member 104 may be considered a second configuration or state (such as that shown at least in FIG. 1D) that permits delivery of a catheter (e.g., catheter 120) from the second lumen 111 to the first lumen 109, e.g., for testing, quality control, or delivery of at least a portion of the catheter into a body of a patient for diagnosis or therapy. Accordingly, in some embodiments, the positioning of the moveable member 110 at the second location 112b relative to the proximal end portion 104a of the elongate member 104 permits delivery of the at least the portion of the catheter 120 (e.g., at least the distal end portion 124b) through both the second lumen 111 and the first lumen 109. For example, in FIG. 1D, relative movement (e.g., translational relative movement along an axis parallel to the X-X axis) between the moveable member 110 and the proximal end portion 104a of the elongate member 104 has positioned the second lumen 111 such that the longitudinal axis 111a of the second lumen 111 is colinear, or approximately colinear, with the longitudinal axis 109a of the first lumen 109 to allow delivery of the at least the portion of the catheter 120 (e.g., at least the distal end portion 124b) through both the second lumen 111 and the first lumen 109. In some embodiments, at least in a state in which the second lumen 111 is positioned at the second location 112b relative to the proximal end portion 104a of the elongate member 104, the second lumen 111 overlaps the first lumen 109 (e.g., as viewed along a viewing direction extending along the longitudinal axis 111a of the second lumen 111 toward the proximal end portion 104a of the elongate member 104) by an amount sufficient to allow delivery of the at least the portion of the catheter 120 (e.g., at least the distal end portion 124b) through both the second lumen 111 and the first lumen 109. According to various embodiments, the second lumen 111 may be positioned more proximally than the first lumen 109.

According to various embodiments, (a) the first relative movement between the moveable member 110 and the proximal end portion 104a of the elongate member 104 (e.g., the sequence of FIG. 1D to FIG. 1C), (b) the second relative movement between the moveable member 110 and the proximal end portion 104a of the elongate member 104 (e.g., the sequence of FIG. 1C to FIG. 1D), or each of (a) and (b) occurs transversely to the longitudinal axis 111a of the second lumen 111. For example, in some embodiments including FIGS. 1C and 1D, the translational relative movement of the moveable member 110 occurs along an axis parallel to axis X-X, which, in some embodiments, may be transverse to the longitudinal axis 111a of the second lumen 111.

As shown in at least FIGS. 1C and 1D, according to some embodiments, the moveable member 110 forms at least part of a siding mechanism that controls fluidic passageway connection states by sliding between one or more passageway ports. The moveable member 110 may be physically coupled to the proximal end portion 104a of the elongate member 104 to selectively provide or not provide access to a port of the first lumen 109 in various manners according to some embodiments.

Figure 2C:
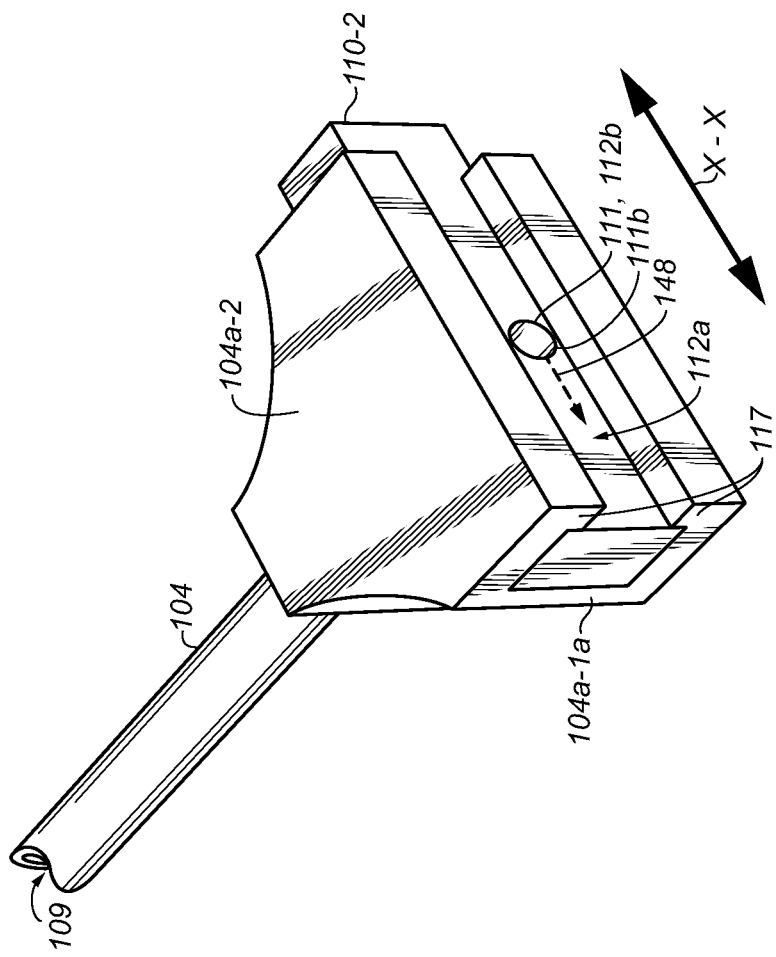
Figure 2E:
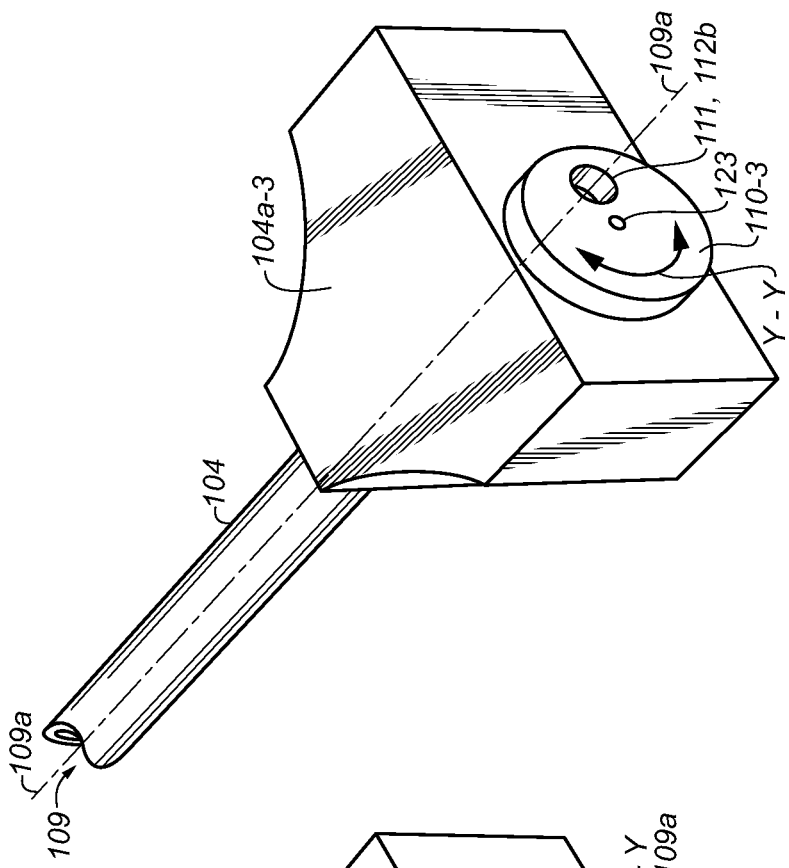
Figure 2D:
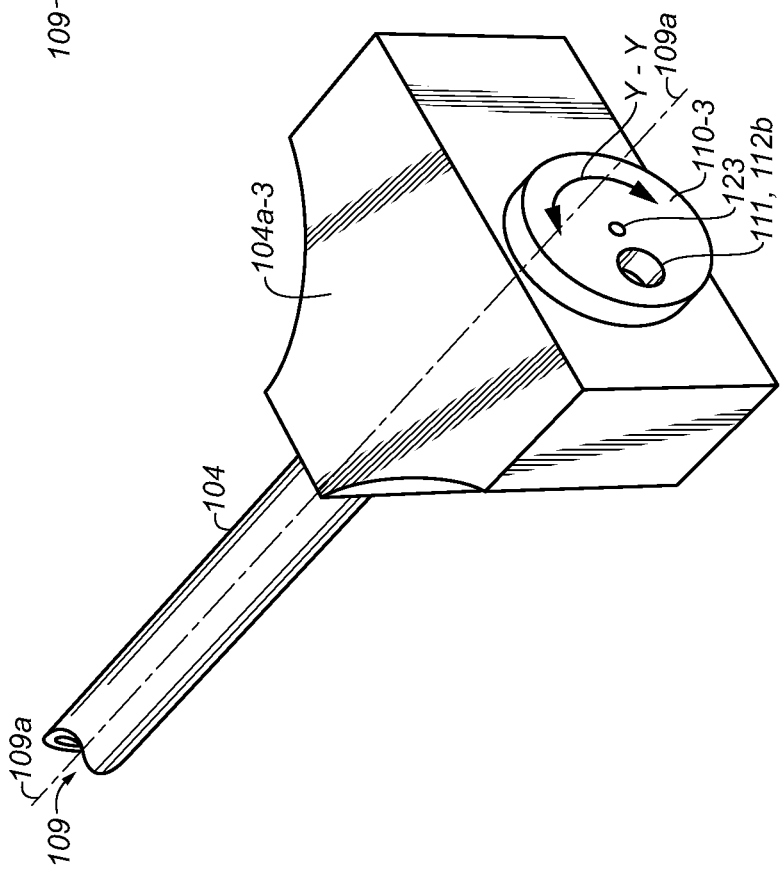

FIGS. 2A-2E illustrate alternate embodiments for the moveable member 110 shown at least in FIGS. 1C and 1D, according to various embodiments of the present invention. In particular, FIGS. 2A and 2B illustrate embodiments of a moveable member 110-1, FIG. 2C illustrates embodiments of a moveable member 110-2, and FIGS. 2D and 2E illustrate alternate embodiments of a moveable member 110-3, as alternate embodiments of moveable member 110, according to various embodiments.

For example, FIGS. 2A and 2B represent some embodiments in which the catheter sheath device 102 includes an elongate member 104 that includes a proximal end portion 104a-1 in which the moveable member 110-1 is disposed proximally-to-distally between particular adjacent portions of the proximal end portion 104a-1 (e.g., sandwiched between particular adjacent portions 104a-1a and 104a-1b of the proximal end portion 104a-1), while allowing relative translational or sliding movement between the moveable member 110-1 and the proximal end portion 104a-1 along an axis parallel to axis X-X. While the particular adjacent portions 104a-1a and 104a-1b of the proximal end portion 104a-1 may limit movement of the moveable member 110-1 to relative movement along an axis parallel to the X-X axis, at least one of the particular adjacent portions 104a-1a and 104a-1b may, in some cases, limit access to the second lumen 111 in the moveable member 110-1. In some example embodiments, the enclosing proximal end portion 104a-1 includes one or more ports 116 (e.g., two ports 116a and 116b are shown in this illustrated embodiment) that allow access of at least a portion of the catheter 120 (e.g., at least the distal end portion 124b) into the second lumen 111 provided in moveable member 110-1. Relative translational or sliding movement between the moveable member 110-1 and the proximal end portion 104a-1 may be employed, according to some embodiments, to position the second lumen 111 at a first location 112a (e.g., FIG. 2A) relative to the proximal end portion 104a-1 that permits delivery of the at least the portion of the catheter 120 (e.g., at least the distal end portion 124b) into the second lumen 111 but not into the first lumen 109 of the elongate member 104. Relative translational or sliding movement between the moveable member 110-1 and the proximal end portion 104a-1 may be employed, according to some embodiments, to position the second lumen 111 at a second location 112b (e.g., FIG. 2B) relative to the proximal end portion 104a-1 that permits delivery of the at least the portion of the catheter 120 (e.g., at least the distal end portion 124b) through both the second lumen 111 and the first lumen 109. Protection against fluid leakage during relative translational or sliding movement between the moveable member 110-1 and the proximal end portion 104a-1 may be employed, according to some embodiments, by, e.g., utilizing one or more seals like first or second seals 142, 141 (i.e., described below in this disclosure) between the moveable member 110-1 and the proximal end portion 104a-1 of the elongate member 104 on the input side of the second lumen 111 (e.g., proximate portion 104a-1b) and the output side of the second lumen 111 (e.g., proximate portion 104a-1a).

In some embodiments, the ports 116a and 116b may be combined into a single port (e.g., a port of elongated or slot-like opening provided in the proximal end portion 104a-1 arranged to provide access to the second lumen 111 of moveable member 110-1). A single port 116 may be advantageous in some embodiments, as it may permit relative movement between the moveable member 110-1 and proximal end portion 104a-1 at least in a particular state in which the at least the portion of the catheter 120 (e.g., at least the distal end portion 124b) is provided in, or otherwise physically constrained in some form of physical engagement with, the second lumen 111 provided in moveable member 110-1. That is, a single port 116 may be employed to overcome a possible impediment to the translational relative movement during the particular state that may be created by a wall portion 116c of the proximal end portion 104a-1 if two ports 116a, 116b were to be instead employed.

It is noted that, in some embodiments, the proximal end portion 104a-1 of the elongate member 104 need not substantially proximally-to-distally surround the moveable member 110-1 (e.g., by way of at least portions 104a-1a and 104a-1b of the proximal end portion 104a-1) as shown in FIGS. 2A and 2B. For example, FIG. 2C illustrates embodiments in which elongate member 104 of the catheter sheath device 102 includes a proximal end portion 104a-2 that physically secures moveable member 110-2 (e.g., at least in part via projections 117) while allowing relative translational or sliding movement between the moveable member 110-2 and the proximal end portion 104a-2 along an axis parallel to axis X-X. At least in this regard, the moveable member 110-2 may be positioned relative to the proximal end portion 104a-2. According to various embodiments, the projections 117 of the proximal end portion 104a-2 physically secure at least in part moveable member 110-2 to the proximal end portion 104a-2 without obstructing any access of at least a portion of the catheter 120 (e.g., at least the distal end portion 124b) to the second lumen 111 provided in the moveable member 110-2 at each of the first location 112a and the second location 112b. (Although FIG. 2C shows the moveable member 110-2 in the second location 112b (i.e., a configuration like that shown in FIGS. 1F and 2B), it can be seen that the second lumen 111 in FIG. 2C would remain accessible throughout a sliding of the moveable member 110-2 in a direction 148 (shown by a broken-line arrow in FIG. 2C) toward the lower-left corner of FIG. 2C to the first location 112a (shown by a broken-line arrow in FIG. 2C).) Protection against fluid leakage during relative translational or sliding movement between the moveable member 110-2 and the proximal end portion 104a-2 may be employed, according to some embodiments, by, e.g., utilizing one or more seals like first or second seals 142, 141 between the moveable member 110-2 and the proximal end portion 104a-2 of the elongate member 104 on the output side of the second lumen 111 (e.g., proximate portion 104a-1a), according to some embodiments.

In some embodiments, the proximal end portion 104a of the elongate member 104 may be physically coupled to the moveable member (e.g., moveable member 110 or moveable member 110-2) as part of a sliding mechanism in which the moveable member (e.g., moveable member 110 or moveable member 110-2) may not be disposed proximally-distally between (e.g., sandwiched between) particular adjacent portions (e.g., portions 104a-1a and 104a-1b in FIGS. 2A and 2B, and portion 104a-1a and projections 117 in FIG. 2C) of the proximal end portion 104a.

In various embodiments, no portion of the catheter sheath device 102 obstructs or prevents delivery of at least a portion of the catheter 120 (e.g., at least the distal end portion 124b) into the second lumen 111 in each of the first location 112a or the second location 112b (for example, as described at least as above in relation to FIG. 1 and FIGS. 2A, 2B, and 2C). That is, in some embodiments, the catheter sheath device 102 may be configured to permit the at least the portion of the catheter 120 (e.g., at least the distal end portion 124b) to be receivable in the second lumen 111 in a state in which the second lumen 111 is positioned at the first location 112a relative to the proximal end portion 104a (including proximal end portion 104a-1 and proximal end portion 104a-2) of the elongate member 104 and in a state in which the second lumen 111 is positioned at the second location 112b relative to the proximal end portion 104a (including proximal end portion 104a-1 and proximal end portion 104a-2) of the elongate member 104. In various embodiments, no portion of the catheter sheath device 102 obstructs or prevents delivery of the at least a portion of the catheter 120 (e.g., at least the distal end portion 124b) into the second lumen 111 throughout a relative movement that positions the second lumen 111 from the first location 112a to the second location 112b, or from the second location 112b to the first location 112a. In some embodiments, the second lumen 111 provides an entry port 111b (reference numeral shown, e.g., in FIGS. 1C, 1D, 2A, 2B, and 2C) configured to permit entry of at least a portion of the catheter 120 (e.g., at least the distal end portion 124b) into the catheter sheath device 102 prior to entry of the at least the portion of the catheter 120 (e.g., at least the distal end portion 124b) into any other port provided by the catheter sheath device 102 at least in a state in which the at least the portion of the catheter 120 (e.g., at least the distal end portion 124b) is being delivered into the catheter sheath device 102. For example, the embodiments associated with FIGS. 1 and 2C are configured to allow direct entry of the catheter 120 into the second lumen 111 provided in the moveable member 110 (including moveable member 110-2) without any prior entry through any other port provided by the catheter sheath device 102. The embodiments associated with FIGS. 2A and 2B, on the other hand, require that the at least the portion of the catheter 120 (e.g., at least the distal end portion 124b) first enter port 116a or port 116b prior to entry into the second lumen 111. In this regard, it is emphasized that ports 116a and 116b are not provided in the moveable member 110-1 according to various embodiments.

It is noted that relative movement between the moveable member 110 (including moveable member 110-1 and moveable member 110-2) and the proximal end portion 104a (including proximal end portion 104a-1 and proximal end portion 104a-2) of elongate member 104 need not be limited to translational relative movement. For example, in some embodiments (a) the "first" relative movement between the moveable member 110 and the proximal end portion 104a of the elongate member 104 that places the second lumen 111 at the first location 112a, or (b) the "second" relative movement between the moveable member 110 and the proximal end portion 104a of the elongate member 104 that places the second lumen 111 at the second location 112b, or each of (a) and (b) includes a rotational relative movement between the moveable member 110 and the proximal end portion 104a of the elongate member 104.

FIGS. 2D and 2E demonstrate various embodiments employing rotational relative movement. FIGS. 2D and 2E include embodiments in which the catheter sheath device 102 includes an elongate member 104 that includes proximal end portion 104a-3 to which the moveable member 110-3 is rotationally coupled via pivot 123. First rotational relative movement (schematically shown by rotational arrows Y-Y) about the pivot 123 allows the second lumen 111 of the moveable member 110-3 to be positioned at the first location 112a (FIG. 2D), and second rotational relative movement (schematically shown by rotational arrows Y-Y) about the pivot 123 allows the second lumen 111 of the moveable member 110-3 to be positioned at the second location 112b (FIG. 2E). Protection against fluid leakage during rotational relative movement between the moveable member 110-3 and the proximal end portion 104a-3 may be employed, according to some embodiments, by, e.g., utilizing one or more seals like first or second seals 142, 141 between the moveable member 110-3 and the proximal end portion 104a-3 of the elongate member 104, according to some embodiments.

Figure 3:
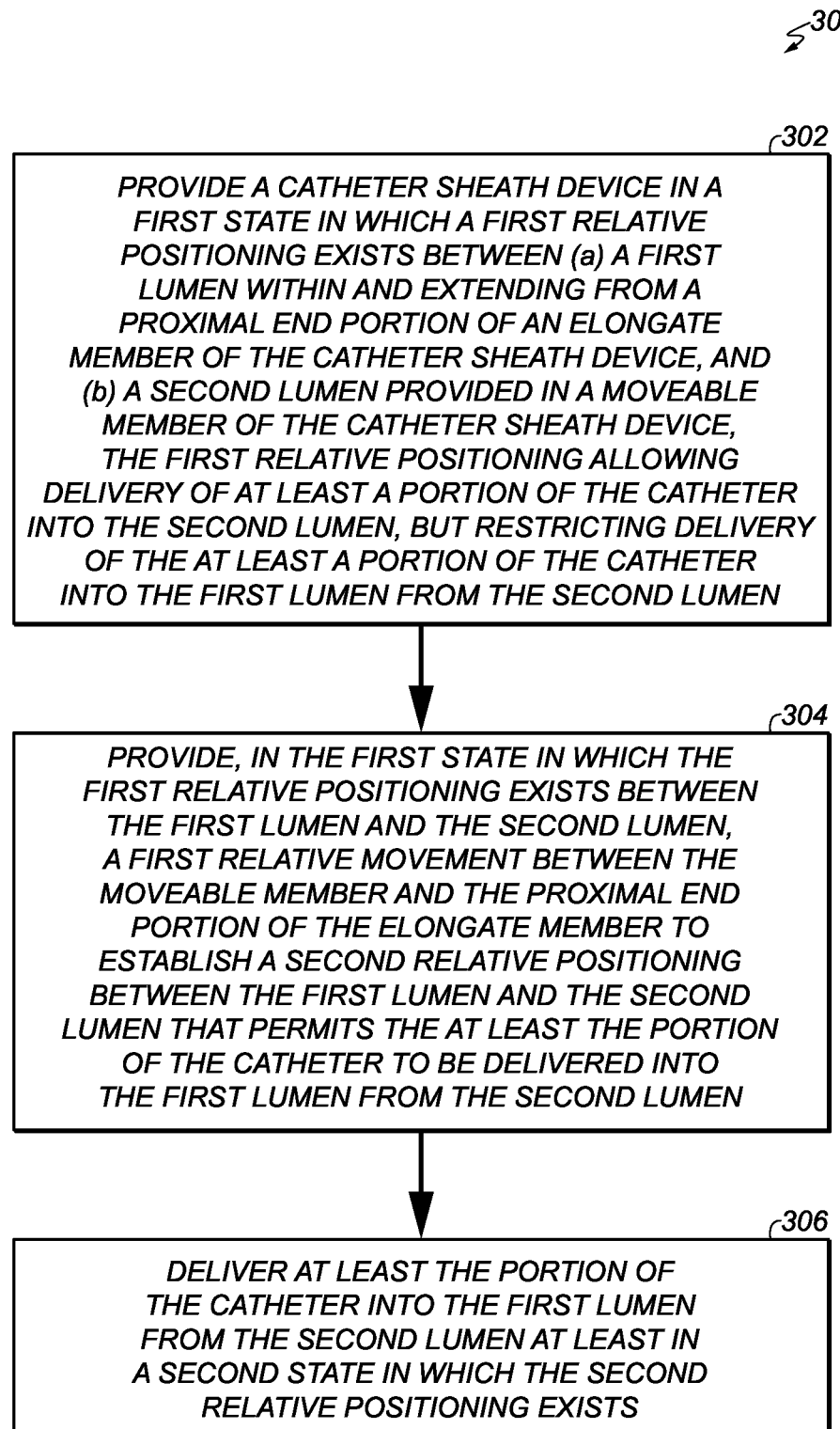
FIG. 3 illustrates a method of delivering a distal end portion of a catheter though at least a portion of a catheter sheath device, according to some embodiments of the present invention.

FIG. 3 is a block diagram representing a method 300 of delivering a distal end portion of a catheter though at least a portion of a catheter sheath device that includes an elongate member, at least a portion of the elongate member configured to be insertable into a body of a patient. Various actions associated with the method 300 are herein described with respect to the catheter device system 100 of FIG. 1 for ease of discussion, but it is understood that other catheter device systems may be employed in other embodiments. It should be noted that various embodiments of the present invention include more or fewer actions and different orderings of actions than those described and illustrated with respect to at least the various blocks of method 300.

Block 302, representing a portion of method 300 according to some embodiments, may include providing the catheter sheath device 102 in a first state in which a first relative positioning exits between (a) a first lumen 109 within and extending from a proximal end portion 104a of the elongate member 104 of the catheter sheath device 102, and (b) a second lumen 111 provided in a moveable member 110 of the catheter sheath device 102 that is physically coupled to the proximal end portion 104a of the elongate member. The first relative positioning allows delivery of at least a portion of a catheter 120 (e.g., at least the distal end portion 124b) into the second lumen 111, and the first relative positioning restricts the at least the portion of the catheter 120 (e.g., at least the distal end portion 124b) from being delivered into the first lumen 109 from the second lumen 111, according to some embodiments. FIG. 1C shows an example of the first relative positioning between the first lumen 109 and second lumen 111, according to some embodiments. It is noted in FIG. 1C that although the distal end portion 124b may be insertable or deliverable into the second lumen 111 during the first relative positioning, the moveable member 110 may be positioned such that no path between the second lumen 111 and the first lumen 109 suitable to allow a delivery of at least the distal end portion 124b of the catheter 120 into the first lumen 109 from the second lumen 111 is provided by the first relative positioning. In some embodiments, in this first relative positioning, the first lumen 109 and the second lumen 111 are fluidically disconnected. In some embodiments, this first relative positioning may be a flushing state, in which the first lumen 109 and the second lumen 111 may be separately flushed.

Block 304, representing a portion of method 300 according to some embodiments, may include providing, in the first state in which the first relative positioning exists between the first lumen 109 and the second lumen 111, a first relative movement between the moveable member 110 and the proximal end portion 104a of the elongate member 104 to establish a second relative positioning between the first lumen 109 and the second lumen 111 that permits the at least the portion of the catheter 120 (e.g., at least the distal end portion 124b) to be delivered into the first lumen 109 from the second lumen 111. For example, according to some embodiments, a first relative movement (e.g., a first relative movement along an axis parallel to the X-X axis) between the moveable member 110 and the proximal end portion 104a of the elongate member 104 may change the first relative positioning between the first lumen 109 and the second lumen 111 as exemplified in at least FIG. 1C to a second relative positioning between the first lumen 109 and the second lumen 111 as exemplified at least in FIG. 1D. In some embodiments, the first relative movement repositions the at least the portion of the catheter 120 (e.g., at least the distal end portion 124b) from a first position (e.g., first location 112a) that does not allow delivery of the portion of the catheter 120 (e.g., at least the distal end portion 124b) into the first lumen 109, such as in a state in which the portion of the catheter 120 is located in the second lumen 111 or, e.g., in a vessel fluidically connected or coupled to the second lumen, during the first relative movement. It is noted that at least the distal end portion 124b of catheter 120 can be delivered into the second lumen 111 and into the first lumen 109 from the second lumen 111 in the second relative positioning exemplified at least in FIG. 1D. In some embodiments, in this second relative positioning, the first lumen 109 and the second lumen 111 are fluidically connected, whereas they are fluidically disconnected in the first relative positioning. In some embodiments, this second relative positioning may be an operative connection state, in which it is possible to deliver at least a portion of the catheter 120 (e.g., at least the distal end portion 124b) from the second lumen 111 into the first lumen 109, and, in some embodiments, into a body of a patient for performing a medical procedure or, in other embodiments, for performing, e.g., training, testing, or quality control of the catheter device system 100.

Block 306, representing a portion of method 300 according to some embodiments, may include, delivering the at least the portion of the catheter 120 (e.g., at least the distal end portion 124b) into the first lumen 109 from the second lumen 111 at least in a second state in which the second relative positioning exists between the first lumen 109 and the second lumen 111 (e.g., as exemplified at least in FIG. 1D). According to some embodiments, the catheter sheath device 102 may be configured to permit delivery of the at least the portion of the catheter 120 (e.g., at least the distal end portion 124b) into the second lumen 111 in each of the first state and the second state.

In some embodiments, the first relative movement, between the moveable member 110 and the proximal end portion 104a of the elongate member 104 from the first relative positioning to the second relative positioning, repositions the at least the portion of the catheter 120 (e.g., at least the distal end portion 124b) relative to the proximal end portion 104a of the elongate member 104. For example, if the at least the portion of the catheter 120 (e.g., at least the distal end portion 124b) is provided in the second lumen 111, or if the at least the portion of the catheter 120 (e.g., at least the distal end portion 124b) is physically constrained in a particular configuration of engagement with the moveable member 110 (e.g., as described below in this disclosure), the first relative movement may reposition the at least the portion of the catheter 120 (e.g., at least the distal end portion 124b) relative to the proximal end portion 104a of the catheter sheath device 102 (for example, as shown in at least FIGS. 1E and 1F described below). In some embodiments, the catheter sheath device 102 may be configured, in a state in which the catheter 120 is coupled to the catheter sheath device 102 to permit entry of at least a portion of the catheter 120 (e.g., at least the distal end portion 124b) into the second lumen 111, to move the at least the portion of the catheter 120 between a first particular location (e.g., a second location 122 in some embodiments) in which the at least the portion of the catheter 120 is positioned to permit entry of the at least the portion of the catheter 120 into the first lumen 109 (e.g., from the second lumen 111), and a second particular location (e.g., a first location 121 in some embodiments) in which the at least the portion of the catheter 120 (e.g., at least the distal end portion 124b) is positioned to prevent or obstruct entry of the at least the portion of the catheter 120 into first lumen 109.

In various embodiments, fluidic communication may be required between various lumens or various ports provided in the catheter sheath device. In some embodiments, the fluidic communication may be required to (a) provide a particular fluid to a patient's body, or (b) extract a particular fluid from the body of a patient, or both (a) and (b). In some embodiments, the fluidic communication may be required to provide fluid (e.g., flushing fluid such as saline or heparinized saline) to flush at least part of the catheter device system 100 of an undesired fluid (e.g., entrapped air or other gases). Accordingly, in some embodiments, fluidic communication between one or more lumens provided in a first part of the catheter sheath device 102 (e.g., moveable member 110) and one or more lumens provided in a second part of the catheter sheath device 102 (e.g., proximal end portion 104a of elongate member 104) may be required. In some embodiments, it may be required that a lumen provided in the first part of the catheter sheath device 102 (e.g., moveable member 110) be in fluid connection or communication with one or more different lumens provided in a second part of the catheter sheath device 102 (e.g., proximal end portion 104a of elongate member 104) in different fluidic connection configurations. In various embodiments where each of the different fluidic connection configurations are defined by different relative positionings between, the first part of the catheter sheath device 102 (e.g., moveable member 110) and the second part of the catheter sheath device 102 (e.g., proximal end portion 104a of elongate member 104), effective fluidic sealing typically may be required therebetween at and during movement between the different relative positionings to at least (a) maintain a desired fluidic communication between the two parts, or (b) restrict the entry of an undesired fluid at an interface between the two parts, or (a) and (b).

Referring back to the exploded view of the catheter sheath device 102 in FIG. 1B, in some embodiments, the catheter sheath device 102 includes a first seal 142 and a second seal 141 that provides or at least facilitates such effective fluidic sealing. According to some embodiments, the first seal 142 may be included as part of the proximal end portion 104a of the elongate member 104, and the second seal 141 may be included as part of the moveable member 110.

The first seal 142 of proximal end portion 104a may include two openings 142a-1 and 142a-2. In a state in which the proximal end portion 104a (e.g., at least the housing 107) is fully assembled with the moveable member 110 physically coupled thereto, the opening 142a-1 may be aligned with the first lumen 109, and the opening 142a-2 may be aligned with the fourth lumen 126 (discussed in more detail below), regardless of the relative-positional-state of the moveable member 110, according to some embodiments.

The second seal 141 of moveable member 110 may include two openings 141a-1 and 141a-2. In a state in which the proximal end portion 104a (e.g., at least the housing 107) is fully assembled with the moveable member 110 physically coupled thereto, the opening 141a-2 may be aligned with the first lumen 109, and the opening 142a-1 may be aligned with the fourth lumen 126 (discussed in more detail below), in a state in which the catheter sheath device system 102 is in the fluidic connection configuration of, e.g., FIGS. 1C and 1E, according to some embodiments. In the fluidic connection configuration of, e.g., FIGS. 1D and 1F, according to some embodiments, the opening 141a-2 may be fluidically sealed or closed by solid portion 142e of first seal 142, and the opening 142a-1 may be aligned with the first lumen 109, according to some embodiments.

In some embodiments, the first seal 142 includes a first sealing surface 142a, and the second seal 141 includes a second sealing surface 141a configured to seal against the first sealing surface 142a to restrict fluid leakage (outward leakage of fluid provided internally in catheter sheath device 102, such as at least from fluidically-connected lumens that are fluidically connected by a particular relative positioning of the moveable member 110 with respect to the proximal end portion 104a of the elongate member 104). For example, the second sealing surface 141a may be positioned to seal against the first sealing surface 142a to restrict fluid leakage at least between the first sealing surface 142a and the second sealing surface 141a at least (a) in a state in which the second lumen 111 is positioned at the second location 112b relative to the proximal end portion 104a of the elongate member, (b) in a state in which the second lumen 111 is positioned at the first location 112a relative to the proximal end portion 104a of the elongate member 104, or (a) and (b). According to various embodiments, the first sealing surface 142a and the second sealing surface 141a are configured to create a fluidic seal between one another to prevent or at least restrict fluid leakage therebetween throughout a relative movement that repositions the second lumen 111 between the first location 112a and the second location 112b.

According to some embodiments, the first sealing surface 142a may include a first opening 142a-1 arranged in fluidic communication with the first lumen 109. According to some embodiments, the second sealing surface 141a may include a second opening 141a-1 arranged in fluidic communication with the second lumen 111. In various embodiments, the first opening 142a-1 may be fluidically disconnected and not in fluidic communication with the second opening 141a-1 at least in a state in which the moveable member 110 is positioned with the second lumen 111 at the first location 112a (e.g., at least FIGS. 1C and 1E) relative to the proximal end portion 104a of the elongate member 104. In various embodiments, the first opening 142a-1 may be arranged in fluidic communication with the second opening 141a-1 in a state in which the moveable member 110 is positioned with the second lumen 111 at the second location 112b (e.g., at least FIGS. 1D and 1F) relative to the proximal end portion 104a of the elongate member 104. According to various embodiments, the first sealing surface 142a may be provided by a surface of the proximal end portion 104a of the elongate member 104. According to various embodiments, the second sealing surface 141a may be provided by a surface of the moveable member 110. In some embodiments, the first sealing surface 142a, the second sealing surface 141a, or each of the first sealing surface 142a and the second sealing surface 141a may be a planar sealing surface (for example, as shown in FIG. 1B).

In some embodiments, the first sealing surface 142a may be provided by a first lubricous polymer layer 142d (e.g., Ultra High Molecular Weight Polyethylene (UHMWPE) or Polytetrafluoroethylene (PTFE)). In some embodiments, the second sealing surface 141a may be provided by a second lubricous polymer layer 141d (e.g., Ultra High Molecular Weight Polyethylene (UHMWPE) or Polytetrafluoroethylene (PTFE)). According to some embodiments, in a state in which the first sealing surface 142a, the second sealing surface 141a, or each of the first and the sealing surfaces 142a, 141a is provided by a lubricious polymer layer (e.g., first lubricious polymer layer 142d, second lubricious polymer layer 141d, respectively), especially a relatively thin (e.g., approximately 1 mm) layer, the generally soft characteristics of a lubricious polymer material such as UHMWPE allow the first sealing surface 142a and the second sealing surface 141a to conform to one another to provide a better seal between the two surfaces. Conforming sealing surfaces 142a, 141a are advantageous in at least some contexts since the surfaces do not need to be machined or molded with substantially matching surfaces to ensure sufficiently intimate contact that may be required to form an effective fluidic seal. These advantages are particularly true when the first and second sealing surfaces 142a, 141a are planar surfaces, that absent any surface compliance would need to be formed with a high degree of flatness to ensure sufficient sealing integrity. Compliant sealing surfaces therefore can be employed to reduce manufacturing costs while providing enhanced seal reliability. The relatively low friction characteristics of materials such as UHMWPE also advantageously reduce the forces required to provide relative movement between the moveable member 110 and the proximal end portion 104a of the elongate member 104.

In some embodiments, the first sealing surface 142a may be provided by first lubricious polymer layer 142d backed by a first elastomeric layer 142c. In some embodiments, the second sealing surface 141a may be provided by second lubricious polymer layer 141d backed by a second elastomeric layer 141c. Various elastomeric materials may be employed according to various embodiments. For example, the present inventors have employed silicone rubber (e.g., approximately 35 durometer) in the first and the second elastomeric layers 142c, 141c. Other elastomers may be employed in other embodiments including solid elastomeric layers and foamed or celled elastomeric layers. According to various embodiments, the elastomeric layers 142c, 141c may be employed for various reasons including acting as backings that allow more uniform pressure to be exerted across a larger portion of the interfaced area between the engaged sealing surfaces 142a, 141a. This allowance of more uniform pressure exertion may be especially important when the first and the second polymer layers 142d, 141d are relatively thin (and consequently, flexible) and, therefore, require that uniform pressure be applied to ensure that a seal is established across as much of the interfaced area between the engaged sealing surfaces 142a, 141a as possible. According to some embodiments, the catheter sheath device 102 may include at least one mechanical spring configured to bias (a) the first sealing surface 142a against the second sealing surface 141a, or (b) the second sealing surface 141a against the first sealing surface 142a. For example, in FIG. 1B, two mechanical springs 144 (e.g., wave spring washers) are employed to provide spring force that biases the second sealing surface 141a against the first sealing surface 142a. In addition or in the alternative, one or more mechanical springs, like mechanical springs 144, may be located on the distal side of the first sealing surface 142a (e.g., toward the first lumen 109, such as at a location between the first sealing surface 142a and the housing 107) to cause a spring force to bias the first sealing surface 142a against the second sealing surface 141a, according to some embodiments. In at least some of such embodiments, the one or more mechanical springs may be placed adjacent or on a rigid member providing a flat surface region to help uniformly distribute the spring force biasing the first sealing surface 142a against the second sealing surface 141a, in the same or similar manner that the inner member 110a helps to uniformly distribute the spring force of the mechanical springs 144 biasing the second sealing surface 141a against the first sealing surface 142a. According to various embodiments, elastomeric layers 142c, 141c act, at least in part, to cause the spring bias force to be more uniformly distributed across the first and second sealing surfaces 142a, 141a, which further improves the fluidic sealing performance of the seals 142 and 141.

According to some embodiments, moveable member 110 may be assembled from multiple parts. For example, in FIG. 1B moveable member 110 includes an inner member 110a and an outer member 110b, according to some embodiments. In some embodiments, inner member 110a may be employed to at least support second lubricious polymer layer 141d and second elastomeric layer 141c. In some embodiments, mechanical springs 144 may be positioned between inner member 110a and outer member 110b to apply the aforementioned bias force. According to some embodiments, moveable member 110 may be physically coupled to the proximal end portion 104a of elongate member 104 via at least one snap-fit projection 110c provided on outer member 110b. According to some embodiments, the at least one snap-fit projection 110c may snap into at least one channel 110d provided in the proximal end portion 104a of the elongate member 104 (e.g., housing 107), the at least one channel position to allow the at least one snap-fit projection 110c to translate therealong during relative movement between the moveable member 110 and the proximal end portion 104a.

In some embodiments, the moveable member 110 includes a third lumen 114 (e.g., FIGS. 1A, 1B, 1C, and 1D) extending through the moveable member 110, the third lumen 114 spaced from the second lumen 111. According to some embodiments, at least in a first state in which the second lumen 111 is positioned at the first location 112a (e.g., at least FIG. 1C) relative to the proximal end portion 104a of the elongate member 104, the third lumen 114 may be positioned in fluidic communication with the first lumen 109. In this regard, according to some embodiments, at least a portion of catheter 120 (e.g., at least distal end portion 124b) is not deliverable into the first lumen 109 from the second lumen 111 in the first state in which the third lumen 114 is fluidically coupled to the first lumen 109.

Figure 1E:
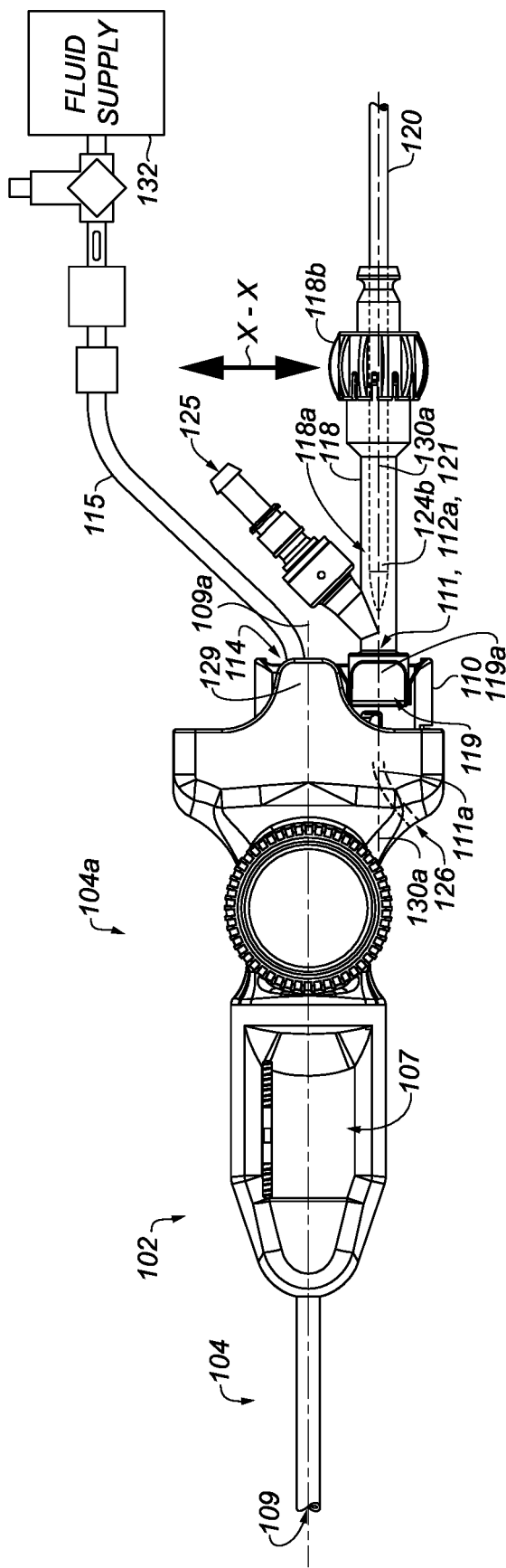
FIGS. 1E and 1F illustrate a sequence of movement of a moveable member of a catheter sheath device including a catheter containing vessel and a fluid conveying line fluidically connected to the moveable member, according to some embodiments of the present invention.

According to some embodiments, fluid may be delivered (e.g., as part of method 300 in a state in which the first relative positioning exists according to block 302) between the first lumen 109 and the third lumen 114 at least in the first state in which the second lumen 111 is positioned at the first location 112a relative to the proximal end portion 104a of the elongate member 104. For example, as shown by at least FIGS. 1C and 1E, the moveable member 110 may be positioned relatively to the proximal end portion 104a of the elongate member such that during the first state, the second lumen 111 is positioned at the first location 112a (e.g., as also shown in FIG. 1C) relative to the proximal end portion 104a of the elongate member 104, and the third lumen 114 is positioned at a location in which it is fluidically coupled to the first lumen 109, according to some embodiments. As shown in FIG. 1E, a fluid conveying line 115 may be fluidically coupled to the third lumen 114 to allow for fluid transfer therebetween according to some embodiments. In some embodiments, fluid may be aspirated from the first lumen 109 via the third lumen 114 in the first state. In some embodiments, fluid may be delivered into the first lumen 109 via the third lumen 114 in the first state. For example, a flushing fluid (e.g., saline or heparinized saline) may be delivered via the fluid conveying line 115 into the third lumen 114, and from there into the first lumen 109 to flush the first lumen 109 of undesired fluid (e.g., air). According to some embodiments, the first lumen 109 may be flushed prior to an insertion into, or delivery through the first lumen 109 by catheter 120. According to some embodiments, the first lumen 109 may be flushed prior to an insertion of at least the elongate member 104 into a body of a patient. According to some embodiments, the first lumen 109 may be flushed prior to an insertion of catheter sheath device 102 into a patient's body.

It is noted according to some embodiments, that at least a portion of the catheter 120 (e.g., at least the distal end portion 124b) is not deliverable into the first lumen 109 from the third lumen 114 at least in the first state in which, in some embodiments, the third lumen 114 is fluidically coupled to the first lumen 109. For example, the third lumen 114 may be sized according to various embodiments to restrict delivery of at least a portion of the catheter 120 (e.g., at least the distal end portion 124b) through the third lumen 114. Additionally, or alternatively, the fluid conveying line 115 may be fixedly coupled to the moveable member 110 (e.g., while concurrently being fluidically coupled to the third lumen 114), the fluid conveying line 115 being configured to restrict insertion of the at least the portion of catheter 120 (e.g., at least the distal end portion 124b) into the third lumen 114, according to some embodiments. According to various embodiments, flushing the first lumen 109 via the third lumen 114 in the first state prior to a subsequent relative movement that repositions the second lumen 111 to second location 112b may be employed to ensure subsequent delivery of at least a portion of the catheter 120 (e.g., at least the distal end portion 124b) (e.g., from the second lumen 111) into the first lumen 109 in a state in which the first lumen 109 is filled with flushing fluid or in which the first lumen 109 is devoid of undesired fluid. According to some embodiments, the second lumen 111 and the third lumen 114 extend through moveable member 110 along parallel directions as shown, e.g., in at least FIGS. 1C and 1E. However, the second lumen 111 and the third lumen 114 may instead extend through moveable member 110 along non-parallel directions in some embodiments.

According to various embodiments, at least in a second state in which the second lumen 111 is positioned at the second location 112b (e.g., at least FIGS. 1D and 1F) relative to the proximal end portion 104a of the elongate member 104, the third lumen 114 may be fluidically disconnected from the first lumen 109. According to some embodiments, at least in the second state in which the second lumen 111 is positioned at the second location 112b relative to the proximal end portion 104a of the elongate member 104, the moveable member 110 may be configured to restrict transfer of fluid between the third lumen 114 and the first lumen 109.

Returning to a discussion of the first state, alternate or additional fluid manipulation operations or methods (e.g., flushing operations) may be conducted according to various embodiments. In some embodiments, various fluid manipulation operations may be conducted in a state in which the second lumen 111 is positioned at the first location 112a relative to the proximal end portion 104a of the elongate member 104 (e.g., the above-discussed first state). Some examples of various fluid manipulation operations or methods are described below.

Figure 4:
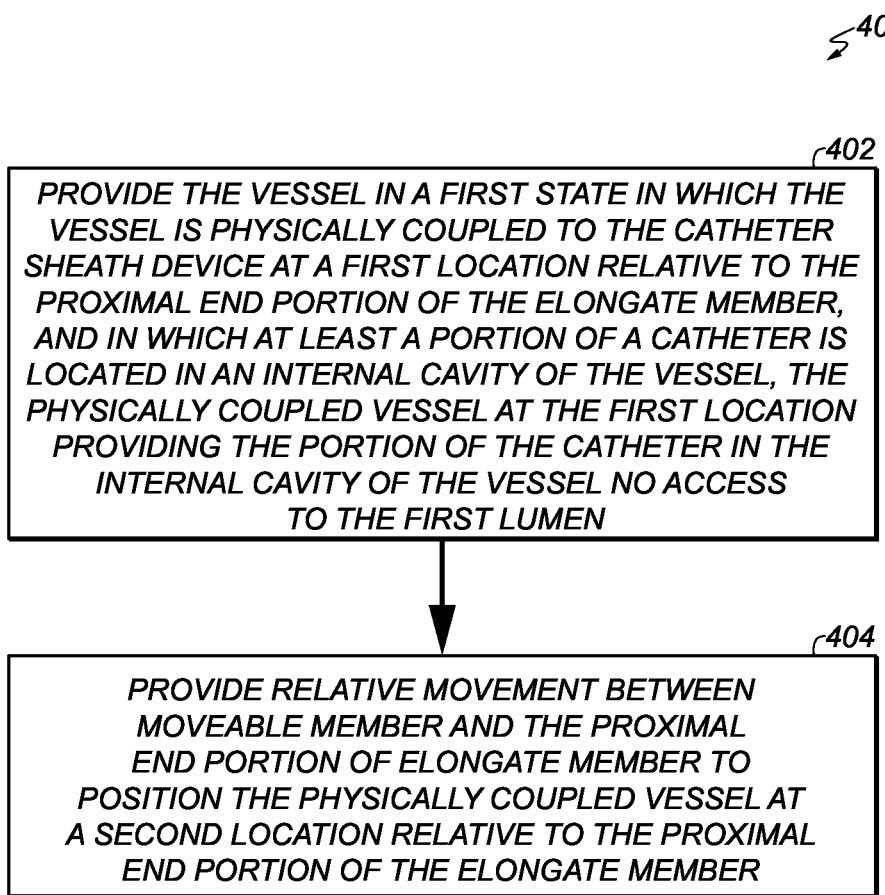
FIG. 4 illustrates a method of providing a vessel with access to a lumen of a catheter sheath device, according to some embodiments of the present invention.

FIG. 4 is a block diagram representing a method 400 of providing a vessel with access to a first lumen of a catheter sheath device, the first lumen within and extending from a proximal end portion of an elongate member of the catheter sheath device. For ease of discussion the catheter sheath device 102 and associated first lumen 109, elongate member 104, and proximal end portion 104a will be discussed in conjunction with method 400, but it is understood that other catheter device systems may be employed in other embodiments. It should be noted that various embodiments of the present invention include more or fewer actions and different orderings of actions than those described and illustrated with respect to at least the various blocks of method 400.

Block 402, representing a portion of method 400 according to some embodiments, may include providing the vessel 118 in a first state in which the vessel is physically coupled to the catheter sheath device 102 at a first location relative to the proximal end portion 104a of the elongate member 104, and in which at least a portion of the catheter 120 (e.g., at least distal end portion 104b) is located in an internal cavity 118a (e.g., shown at least in FIGS. 1E and 1F) of the vessel 118, the physically coupled vessel at the first location 112a providing the portion of the catheter 120 in the internal cavity 118a of the vessel 118 no access to the first lumen 109. For example, in FIGS. 1E and 1F, vessel 118 may be physically coupled to the catheter sheath device 102. According to some embodiments, physical coupling of vessel 118 to the catheter sheath device 102 occurs at a place where the catheter sheath device 102 is employed to perform a medical diagnostic or medical treatment procedure. According to some embodiments, physical coupling of vessel 118 to the catheter sheath device 102 occurs at a place other than a place where the catheter sheath device 102 is employed to perform a medical diagnostic or medical treatment procedure. For example, vessel 118 may be physically coupled the catheter sheath device 102 at a place of (a) the manufacturing or assembly of some portion of the catheter sheath device 102, (b) the manufacturing or assembly of some portion of the vessel 118, or both (a) and (b). In some embodiments, vessel 118 may be physically coupled to the catheter sheath device 102 at a particular location located closer to the proximal end portion 104a of elongate member 104 than the distal end portion 104b of the elongate member 104. In some embodiments, vessel 118 may be physically coupled to the moveable member 110. In some embodiments, vessel 118 may be fixedly coupled to the catheter sheath device 102. In some embodiments, vessel 118 may be removable or detachably couplable to the catheter sheath device 102.

For example, according to some embodiments, a coupling 119 (FIGS. 1A, 1E) provided by vessel 118 allows vessel 118 to be removably couplable to a protrusion 119b (FIGS. 1C, 1D) provided by catheter sheath device 102 (e.g., provided on moveable member 110). Coupling 119 may be provided by a medical quick disconnect coupling according to some embodiments. According to some embodiments, once coupled to catheter sheath device 102, vessel 118 can be decoupled from catheter sheath device 102 by activating coupling release member 119a (FIGS. 1A, 1E). According to some embodiments, coupling release member 119a may be implemented as a medical quick disconnect coupling, known in the art, such as 20AC SERIES—ACETAL QUICK COUPLINGS provided by Industrial Specialties Mfg. & IS MED Specialties, 4091 So. Eliot St., Englewood, CO 80110-4396. According to some embodiments, coupling 119 may be provided by catheter sheath device 102 and protrusion 119b may be provided by vessel 118.

According to various embodiments, second lumen 111 may be provided in protrusion 119b. Various seals may be associated with (a) protrusion 119b, (b) coupling 119, or (a) and (b) to provide a substantially leak-free coupling between vessel 118 and a least a portion of the catheter sheath device (e.g., second lumen 111). For example, a seal 119c (FIGS. 1C, 1D) may be provided on protrusion 119b, according to some embodiments. The use of a vessel 118 that is removable or detachably couplable to catheter sheath device 102 may be motivated for various reasons, including facilitating exchanges between different catheters as described below. It is noted that other types of releasable/detachable couplings may be employed according to other embodiments.

In some embodiments, in the first state associated with block 402, the physically coupled vessel may be provided at a first location relative to the proximal end portion 104a of the elongate member 104. For example, the physically coupled vessel 118 may be positioned at a first location 121 (e.g., at least FIG. 1E) relative to the proximal end portion 104a of elongate member 104. According to some embodiments, first location 121 may be provided by first location 112a described above. According to some embodiments, the physically coupling the vessel 118 to the catheter sheath device 104 associated with block 402 includes physically coupling the vessel 118 at the first location 121. According to various embodiments, vessel 118 includes at least one internal cavity (e.g., internal cavity 118a (e.g., at least FIGS. 1E and 1F)).

In some embodiments, in the first state associated with block 402, at least a portion of a catheter (e.g., catheter 120) may be provided in the internal cavity 118a of vessel 118. The internal cavity 118a may be sufficiently sized to retain at least a portion of the catheter 120 in a state in which the portion of the catheter 120 is in its delivery configuration, but not in a state in which the portion of the catheter 120 is in its deployed or expanded configuration. For example, the internal cavity 118a of the vessel 118 may be insufficiently sized to permit the distal end portion 124b of the catheter 120 to be provided therein in a state in which the distal end portion 124b is in its deployed or expanded configuration, but the internal cavity 118a of the vessel 118 may be sufficiently sized to permit the distal end portion 124b of the catheter 120 to be provided therein in a state in which the distal end portion 124b is in its delivery configuration. U.S. Pat. No. 9,452,016, issued Sep. 27, 2016 provides an example of catheter 120, according to some embodiments.

According to various embodiments, the physically coupled vessel at the first location 121 provides the portion of the catheter 120 in the internal cavity 118a of vessel 118 no access to the first lumen 109. According to various embodiments, the physically coupled vessel at the first location 121 positions the second lumen 111 at the first location 112a relative to the proximal end portion 104a of the elongate member 104, such that delivery of at least the portion of the catheter 120 into the second lumen 111 is physically permitted, but delivery of at least the portion of the catheter 120 into the first lumen 109 from the second lumen 111 is not physically permitted. According to some embodiments, the at least the portion of the catheter 120 may be provided in the internal cavity 118a of the vessel 118 after the vessel 118 has been physically coupled to the catheter sheath device 102.

According to some embodiments, the at least the portion of the catheter 120 may be provided in the internal cavity 118a of the vessel 118 before the vessel 118 has been physically coupled to the catheter sheath device 102. Providing the at least the portion of the catheter 120 in the internal cavity 118a of the vessel 118 before the vessel 118 has been physically coupled to the catheter sheath device 102 may be motivated for different reasons. For example, in some embodiments, the at least the portion of the catheter 120 may have been a portion of the catheter 120 that was previously processed in a particular manner to achieve a desired state. Once processed in the particular manner, providing the portion of the catheter 120 in internal cavity 118a of vessel 118 may be employed to help maintain the desired state of the portion of the catheter 120 during a subsequent engagement or interaction with the catheter sheath device 102. For example, the at least the portion of the catheter 120 may be a particular portion (e.g., at least the distal end portion 124b) that was flushed in a previous flushing operation of undesired fluids such as air. Providing the flushed portion of the catheter 120 in the internal cavity 118a of vessel 118 (especially in a state in which the internal cavity 118a contains a medium (e.g., a fluid such as saline) in sufficient quantity to reduce exposure to undesired fluids) can avoid contamination of the previously flushed catheter portion prior to a subsequent engagement or interaction with the catheter sheath device 102. Some examples of providing a flushed catheter can be found in International Publication No. WO2017/124169, which published on Jul. 27, 2017.

According to various embodiments, vessel 118 may contain a fluid in the internal cavity 118a, at least in a state in which the physically coupled vessel 118 is positioned at the first location 121. According to various embodiments, the fluid may be a flushing fluid (e.g., saline or heparinized saline) or a fluid or medium employed to restrict contamination by, or exposure to, an undesired environment. In some embodiments, fluid may be located in the internal cavity 118a of the vessel 118 while or during a physical coupling the vessel 118 to the catheter sheath device 102. In some embodiments, the at least the portion of the catheter 120 may be located in the internal cavity 118a of the vessel 118 while or during a physical coupling the vessel 118 to catheter sheath device 102. In some embodiments, the portion of the catheter 120 located in the internal cavity 118a of the vessel 118 may be wetted by the fluid located in the internal cavity 118a. In some embodiments, the portion of the catheter 120 located in the internal cavity 118a of the vessel 118 may be submerged in the fluid located in the internal cavity 118a. In some embodiments, the fluid located in the internal cavity 118a of the vessel 118 may substantially fill an entirety of the internal cavity 118a (e.g., in conjunction with the at least the portion of the catheter 120). In some embodiments, only or substantially only a single fluid substance may be located in the internal cavity 118a of the vessel 118. For example, in the case where the fluid is saline, the internal cavity 118a contains or substantially contains only saline as a fluid, and any other fluid present in the saline is present at a proportion less than that which would be harmful if entered into a patient's body with the saline, according to some embodiments. In some embodiments, a fluid other than air may be located in the internal cavity 118a of the vessel 118.

According to various embodiments, the internal cavity 118a of the physically coupled vessel 118 at the first location 121 may be fluidically disconnected from the first lumen 109, which extends through the elongate member 104 of the catheter sheath device 102. For example, a seal provided by first and second sealing surfaces 142a, 141a (FIG. 1B) may be employed to fluidically disconnect the physically coupled vessel 118 at the first location 121 from the first lumen 109. In some embodiments, while fluid may not flow between the physically coupled vessel 118 at the first location 121 and the first lumen 109, fluid may still flow through first lumen 109 via other mechanisms. For example, according to some embodiments, method 400 may include (e.g., as part of block 402) conveying fluid between a fluid supply 132 and the first lumen 109 in a state in which the physically coupled vessel 118 is at the first location 121. For example, the fluid conveyed between the fluid supply 132 and the first lumen 109 in a state (e.g., the first state associated with block 402) in which the physically coupled vessel 118 is at the first location 121 may be via the third lumen 114 (e.g., as described above in this disclosure, such as via fluid conveying line 115). In some embodiments, the conveying the fluid between the fluid supply 132 and the first lumen 109 includes conveying the fluid through a particular lumen (e.g., third lumen 114) provided in the moveable member 110. According to some embodiments, the particular lumen may be fluidically disconnected from the internal cavity 118a of the vessel 118 at least in a state (e.g., the first state associated with block 402) in which the physically coupled vessel 118 is at the first location 121. For example, in the first configuration or state of FIG. 1E, the third lumen 114 may be fluidically disconnected from the internal cavity 118a of the vessel 118. In some embodiments, the fluid supply 132 may be fluidically disconnected from the internal cavity 118a of the vessel 118 during the conveying the fluid between the fluid supply 132 and the first lumen 109.

According to some embodiments, fluid movement into, or out of, or both into and out of the internal cavity 118a of the vessel 118 may occur in a state in which the physically coupled vessel 118 is at the first location 121. Such fluid movement may be motivated for various reasons. For example, although the at least the portion of the catheter 120 (e.g., at least the distal end portion 124b) may be provided in fluid in the internal cavity 118a of the vessel 118 (e.g., an amount of fluid sufficient to prevent the at least the portion of the catheter from being exposed to an undesired fluid such as air) prior to, or during the physical coupling of the vessel 118 to the catheter sheath device 102, the act of physically securing the vessel 118 to the catheter sheath device 102 may itself introduce some (usually a small amount) of undesired fluid into the internal cavity 118a. According to some embodiments, additional flushing may be required to remove any undesired fluid that may exist in the internal cavity 118a after the physical coupling of the vessel 118 to the catheter sheath device 102 as per block 402. In some embodiments, fluid may be introduced via port 125 (FIGS. 1E, 1F) into the internal cavity 118a of the physically coupled vessel 118. The introduced fluid may be, according to some embodiments, a flushing fluid such as saline or heparinized saline that may be used to flush or expel any undesired fluid from the vessel 118. Typically, the undesired fluid may be primarily or substantially located proximate an interface between the catheter sheath device 102 and the physically coupled vessel 118, e.g., where undesired air may be introduced during the physical coupling of the vessel 118 to the catheter sheath device 102. According some embodiments, at least some of the flushing fluid that is introduced via port 125 into the internal cavity 118a of vessel 118, and at least some of any pre-existing fluid in the internal cavity 118a and any undesired fluid present in the internal cavity 118a, may be flushed out of the internal cavity 118a via a fourth lumen 126 provided in the catheter sheath device 102.

Figure 1F:
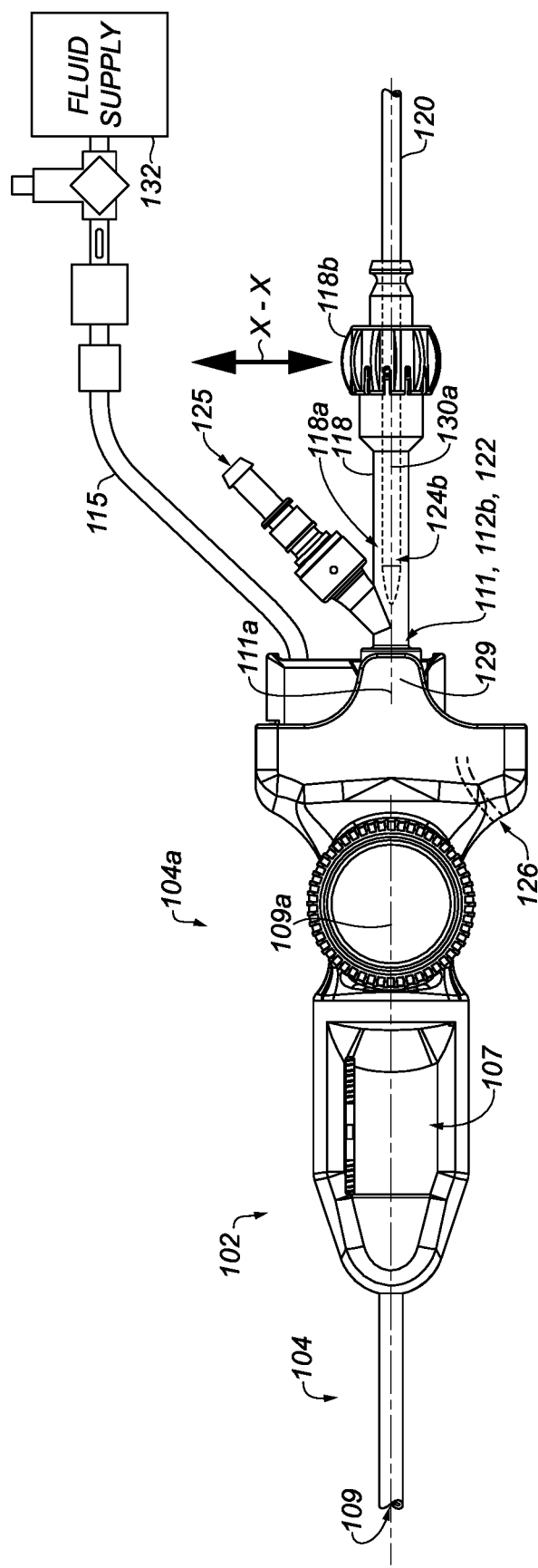

The fourth lumen 126, according to some embodiments, is referenced in FIG. 1D, and its internal location in and exit location from housing 107 are shown by broken lines in FIGS. 1E and 1F. In some embodiments, the fourth lumen 126 may be positioned to be in fluidic communication with the internal cavity 118a of the vessel 118 in a state in which the physically coupled vessel 118 is located at the first location 121. In some embodiments, the fourth lumen 126 may be provided in the proximal end portion 104a of elongate member 104. In some embodiments, the fourth lumen 126 provides a pathway for fluid in the physically coupled vessel 118 to flow through a portion of the catheter sheath device 102 (e.g., a portion of the housing 107) to a location where it may be expelled from the portion of the catheter sheath device 102. According to various embodiments, the proximal end portion 104a of the elongate member 104 comprises fourth lumen 126, which may extend into, and in some embodiments, through the proximal end portion 104a of the elongate member 104. According to various embodiments, the fourth lumen 126 may be spaced from the first lumen 109 (for example, as shown in at least FIGS. 1D, 1E, and 1F). According to some embodiments, the fourth lumen 126 and the first lumen 109 are fluidically disconnected. According to some embodiments, at least in a state in which the second lumen 111 provided in moveable member 110 is positioned at first location 112a relative to the proximal end portion 104a of the elongate member 104, the second lumen 111 may be positioned to be in fluidic communication with the fourth lumen 126. On the other hand, according to some embodiments such as those illustrated by FIGS. 1D and 1F including a state in which the second lumen 111 provided in moveable member 110 is positioned at second location 112b relative to the proximal end portion 104a of the elongate member 104, the second lumen 111 may be fluidically disconnected from the fourth lumen 126. It is noted that, in some embodiments, the configuration of the moveable member 110 prevents any fluidic connection between the fourth lumen 126 and the third lumen 114. Such a configuration may be motivated by various reasons including, for instance, separating flushing functionality from operative functionality, to help ensure that undesired fluid is not introduced, according to some embodiments. For example, the third lumen 114 and the fourth lumen 126 may be configured for fluid flushing in the flushing configuration or state of FIGS. 1C and 1E prior to moving the catheter sheath device 102 into its operative configuration or state of FIGS. 1D and 1F, according to some embodiments. For instance, in the flushing configuration or state of FIGS. 1C and 1E, the fourth lumen 126 may be configured (e.g., at least via its fluidic connection to the second lumen 111 in this state) to flush the vessel 118 of undesired fluid, while the third lumen 114 may be configured (e.g., at least via its fluidic connection with the first lumen 109 in this state) to flush the first lumen 109 of undesired fluid, according to some embodiments. Then, in a state in which the respective flushing procedures are completed, the catheter sheath device 102 may be safely transitioned into the operative configuration or state of FIGS. 1D and 1F with little or no introduction of undesired fluid, e.g., at least by way of the various seals, surfaces, and springs discussed above with respect to FIG. 1B, according to some embodiments.

In this regard, according to various embodiments, the fourth lumen 126 and the third lumen 114 are fluidically disconnected. In some embodiments, the fourth lumen 126 may be fluidically disconnected from the third lumen 114 regardless of any particular relative positioning between the second lumen 111 and the proximal end portion 104a of the elongate member 104 regardless of whether the catheter sheath device 102 is in the fluidic connection configuration or state of FIG. 1D or the fluidic connection configuration or state of FIG. 1E. In some embodiments, at least in a state in which the second lumen 111 is positioned at the second location 112b relative the proximal end portion 104a of the elongate member 104, and at last in a state in which the second lumen 111 positioned at the first location 112a relative to the proximal end portion 104a of the elongate member 104, the fourth lumen 126 and the third lumen 114 are fluidically disconnected (for example, as shown in at least FIGS. 1C and 1D).

Referring back to FIG. 3, but with reference to some embodiments including fourth lumen 126, method 300 may include delivering fluid into the fourth lumen 126 from the second lumen 111 at least in a state (e.g., the first state associated with block 302) in which, e.g., the second lumen 111 may be positioned at the first location 112a relative to the proximal end portion 104a of the elongate member 104, as shown, for instance in FIGS. 1C and 1E. According to some embodiments, the second lumen 111 may be fluidically disconnected from the fourth lumen 126 at least in a state (e.g., the second state associated with block 306) in which, e.g., the second lumen 111 may be positioned at the second location 112*b* relative to the proximal end portion 104*a* of the elongate member 104, as shown, for instance in FIGS. 1D and 1F.

According to some embodiments, the fourth lumen 126 may be sized to restrict delivery of at least the distal end portion 124*b* of catheter 120 through the fourth lumen 126. For example, in some embodiments, the fourth lumen 126 may be configured to allow only fluid flow therethrough, and limiting a size of the fourth lumen 126 to not allow delivery of at least the distal end portion 124*b* of catheter 120 therethrough may be employed as a way of preventing a user from inserting at least the distal end portion 124*b* of catheter 120 into an incorrect lumen of the catheter sheath device 102.

It is noted in various embodiments, that vessel 118 may be flushed of undesired fluid by additional or alternate structures other than the fourth lumen 126. For example, in some embodiments, any residual undesired fluid in the internal cavity 118*a* of vessel 118 may be expelled proximally (for example, as fluid is supplied via port 125) by releasing valve 118*b* on vessel 118. According to some embodiments, valve 118*b* may be a collet-type valve that, when turned in one direction, increases a sealing action against an external surface of catheter 120, and, when turned in the other direction, reduces a sealing action against the external surface of catheter 120 thereby allowing for fluid escape.

Referring back to FIG. 4, block 404 represents a portion of method 400, according to some embodiments, and may include providing relative movement between a moveable member (e.g., moveable member 110) and the proximal end portion 104*a* of the elongate member 104 to position the physically coupled vessel 118 at a second location 122 relative to the proximal end portion 104*a* of the elongate member 104, the moveable member (e.g., moveable member 110) physically coupled to the proximal end portion 104*a* of the elongate member 104. According to some embodiments, second location 122 may be provided by second location 112*b* described above. According to some embodiments, the second location 122 is other than the first location 121 described above with respect to at least block 402 of FIG. 4. According to some embodiments, the physically coupled vessel 118 at the second location 122 provides the portion of the catheter (e.g., at least the distal end portion 124*b*) in the internal cavity 118*a* of the vessel 118 access to the first lumen 109. In some embodiments, the portion of the catheter (e.g., at least the distal end portion 124*b*) in the internal cavity 118*a* of the vessel 118 has access to the first lumen 109 via the second lumen 111 in a state in which the physically coupled vessel 118 is at second location 122. According to various embodiments, the vessel 118 may contain fluid in the internal cavity 118*a* of the vessel 118, the internal cavity 118*a* of the physically coupled vessel 118 at first location 121 may be fluidically disconnected from the first lumen 109, and the internal cavity 118*a* of the physically coupled vessel 118 at the second location 122 may be fluidically connected to the first lumen 109. For example, in FIG. 1F, the physically coupled vessel 118 has been relatively moved (e.g., along an axis parallel to axis X-X) from first location 121 to second location 122 in which the portion of the catheter (e.g., at least the distal end portion 124*b*) in the internal cavity 118*a* of the vessel 118 now has access to the first lumen 109. In some embodiments, this transition (e.g., from FIG. 1E to FIG. 1F) signifies a transition of the catheter sheath device 102 from a flushing configuration or state to an operative configuration or state, the operative configuration or state being one in which the catheter 120 may be introduced into the first lumen 109 and, in some embodiments, subsequently into a body of a patient. In some embodiments, the portion of the catheter (e.g., distal end portion 124*b*) in the internal cavity 118*a* of the vessel 118 has access to the first lumen 109 via the second lumen 111 when the physically coupled vessel 118 is at second location 122.

According to various embodiments, the vessel 118 contains fluid in the internal cavity 118*a* of the vessel 118, and the internal cavity 118*a* of the physically coupled vessel 118 at first location 121 is fluidically disconnected from the first lumen 109, and the internal cavity 118*a* of the physically coupled vessel 118 at the second location 122 is fluidically connected to the first lumen 109

Repositioning the physically coupled vessel 118 between two locations (e.g., first location 121 and second location 122) may be motivated for different reasons. For example, according to some embodiments, in a state in which the physically coupled vessel 118 is flushed of undesired fluids (e.g., air) at the first location 121 (e.g., as described in this disclosure), a subsequent repositioning of the physically coupled vessel 118 to second location 122 advantageously reduces an amount of additional flushing that is required since the physically coupled vessel 118 has already been flushed. If the vessel 118 was primarily flushed at the second location 122, undesired fluid could be delivered into the first lumen 109 which could subsequently adversely affect a patient. Further advantages occur when a first catheter is required to be exchanged with a second catheter. Exchanging the first catheter with the second catheter at the second location 122*b* could introduce undesired fluid (e.g., air) into the first lumen 109. Moving the physically coupled vessel 118 from the second location 122 back to the first location 121 and exchanging the first catheter with the second catheter at the first location 121 reduces the risk of introducing undesired fluid into the first lumen 109. Flushing the second catheter at the first location 121 allows the second catheter to be subsequently moved to a location suitable for access to the first lumen 109 (e.g., second location 122), while reducing the risk of introducing undesired fluid in to the first lumen 109. It is noted, in some embodiments, that the exchange between the first catheter and the second catheter at the first location 121 may involve removing the first catheter from vessel 118 (for example, at least in part by releasing valve 118*b*) and then inserting the second catheter into the vessel 118 and then flushing the inserted second catheter. In some embodiments, the exchange between the first catheter and the second catheter at the first location 121 may include physically decoupling the vessel 118 from the catheter sheath device 102, and then physically coupling a second vessel to the catheter sheath device 102, a portion of the second catheter located in the second vessel during the physical coupling of the second vessel. Such embodiments may be advantageous as it may allow the second catheter to be presented to the catheter sheath device 102 in a flushed or substantially flushed condition protected by the second vessel, thereby reducing the overall flushing burden. It is noted that in some embodiments, a portion of the first catheter may remain in the vessel 118 at least during the physical decoupling of vessel 118 from the catheter sheath device while in some embodiments, a portion of the first catheter may be removed from the vessel 118 before, during, or after the physical decoupling of vessel 118 from the catheter sheath device. According to various embodiments employing intimately contacting sliding surfaces (e.g., first and second sealing surfaces 142*a*, 141*a*) between the moveable member 110 and the proximal end portion 104*a* of the elongate member 104, the intimately contacting sliding surfaces can be employed to reduce the ingress of undesired fluid into the physically coupled vessel as it is moved between the first location 121 and the second location 122.

According to some embodiments, method 400 includes, e.g., upon conclusion of the actions of block 404, delivering the portion of the catheter (e.g., at least the distal end portion 124b) into the first lumen 109 from the internal cavity 118a of the physically coupled vessel 118 located at the second location 122. In some embodiments, the portion of the catheter in the internal cavity 118a of the vessel 118 may be a distal end portion 124b of the catheter, and the method 400 may include delivering the catheter 120 distal-end-portion-first into the first lumen 109 in a state in which the physically coupled vessel 118 is at the second location 122. Various embodiments employing flushing techniques as described in this disclosure allow portions of the catheter 120 to be delivered into the first lumen 109 while reducing occurrences in which undesired fluid (e.g., air) may be introduced into the catheter sheath device 102.

In some embodiments, the catheter sheath device 102 may be configured to restrict or prevent relative movement between the moveable member 110 and the proximal end portion 104a of the elongate member 104 in absence of a physical coupling of the vessel 118 to the catheter sheath device 102, e.g., per block 402, at least in a first configuration of engagement between the catheter 120 and the catheter sheath device 102, such as the first configuration of engagement shown in FIG. 1E. For example, an interlock may be employed according to some embodiments. For example, in FIGS. 1B, 6A, and 6B, catheter sheath device 102 includes an interlock 127 (also referred to as an interlock mechanism) configured to prevent or at least restrict relative movement between the moveable member 110 and the proximal end portion 104a of the elongate member 104 at a particular relative positioning between the two in absence of a physical coupling between the vessel 118 and the proximal end portion 104a of the elongate member 104.

Figure 6A:
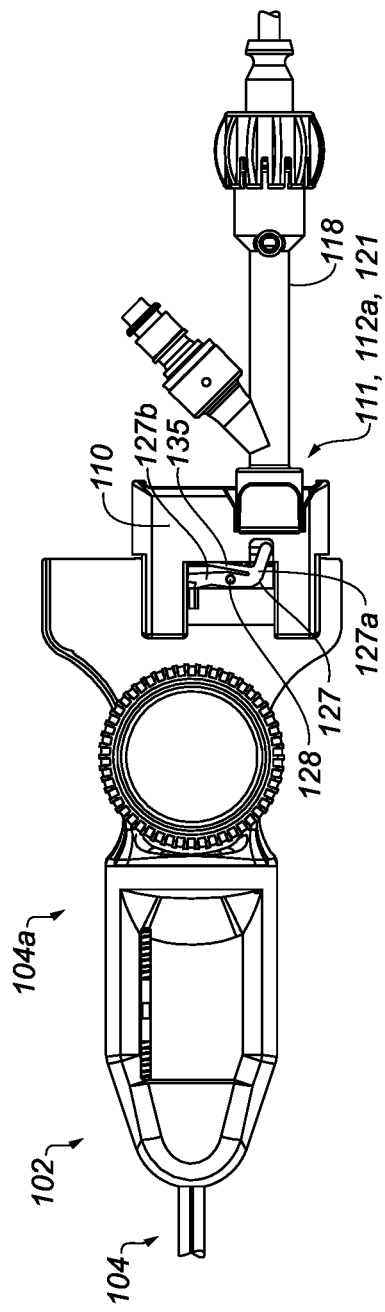
FIGS. 6A and 6B illustrate operation of an interlock mechanism of a catheter sheath device, according to some embodiments of the present invention.
Figure 6B:
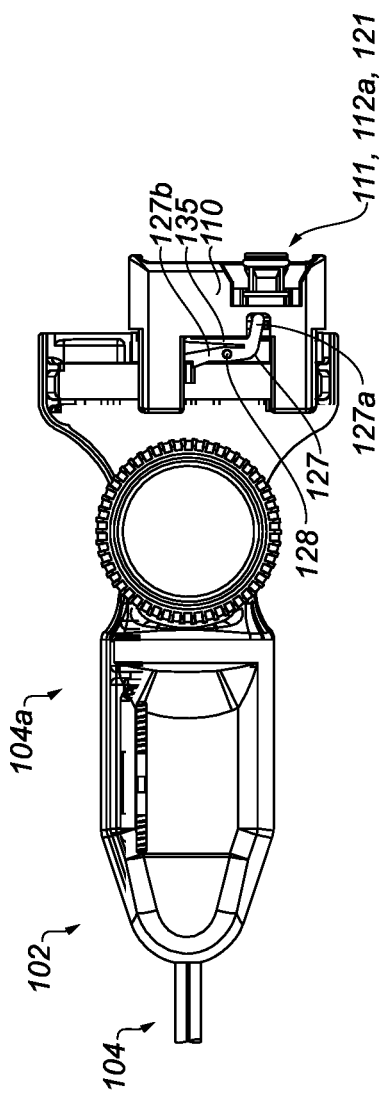
Figure 7A:
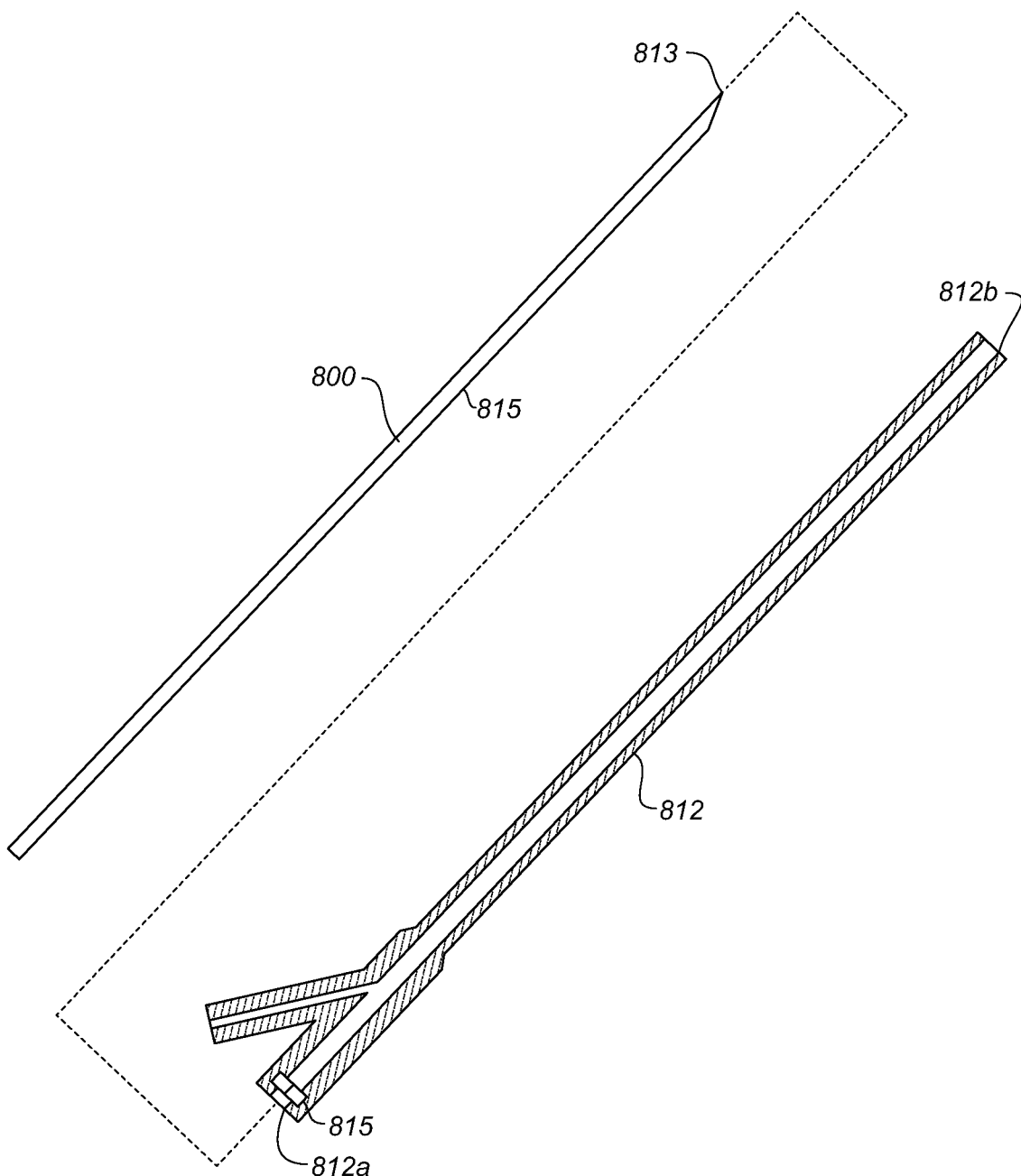
FIG. 7A is a schematic that shows at least part of a conventional catheter system.
Figure 7B:
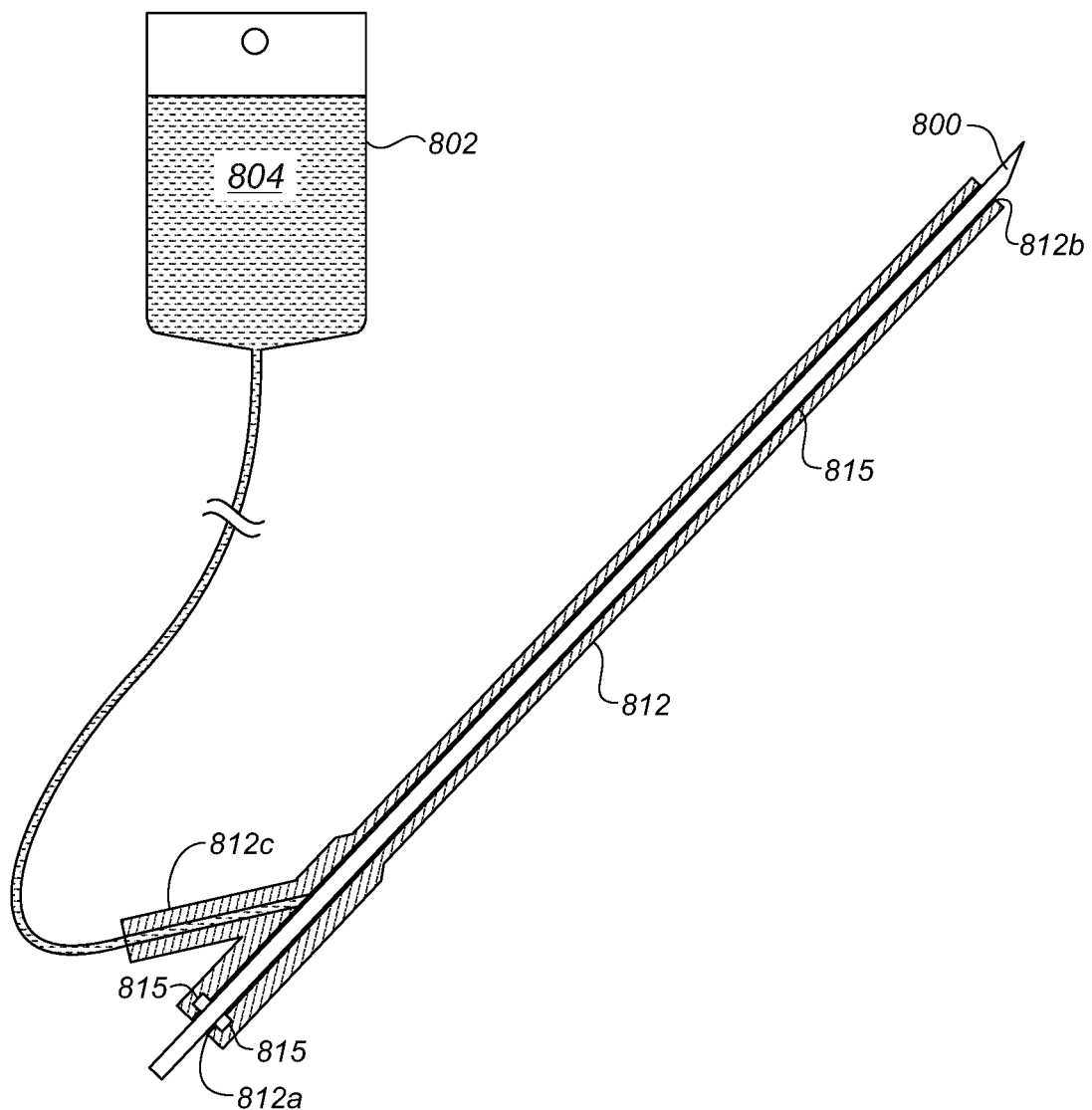
FIG. 7B illustrates a typical flushing procedure employed by a conventional catheter system.

For example, FIG. 6A illustrates operation of the interlock 127 in a state in which the vessel 118 is physically coupled to the catheter sheath device 102 via moveable member 110, and FIG. 6B illustrates a state in which the vessel 118 is physically disconnected from the catheter sheath device 102. It is noted that a portion of the catheter sheath device 102 is shown in a partial section view to show interlock 127 in FIGS. 6A and 6B. In some embodiments according to FIGS. 6A and 6B, the interlock 127 may be configured to rotate about a pivot 128 between an engaged state in which the vessel 118 is physically disconnected from the catheter sheath device 102 (illustrated by FIG. 6B), and a disengaged state in which the vessel 118 is physically coupled to the catheter sheath device 102 moveable member 110 (illustrated by FIG. 6A). In some embodiments according to FIGS. 6A and 6B, the interlock 127 includes a spring-like portion 135 that provides a biasing force to cause the jaw 127b of interlock 127 to engage against the proximal end portion 104a of elongate member 104 and thereby restrict or prevent relative movement between the moveable member 110 and the proximal end portion 104a. In some embodiments, the interlock 127 includes a release arm 127a. In some embodiments, the release arm 127a may be engaged during the physical coupling of the vessel 118 to the proximal end portion 104a of the elongate member 104, which is illustrated, for example, by the sequence of FIG. 6B to FIG. 6A (showing the coupling of the vessel 118 at the first location 121). According to some embodiments, such engagement of the release arm 127a releases the interlock 127 (e.g., by pivoting interlock jaw 127b away from engagement with the proximal end portion 104a) and permits relative movement between the moveable member 110 (with its physically coupled vessel 118) and the proximal end portion 104a of the elongate member 104 (e.g., the moveable member is able to move from the first location 121 toward the second location 122 relative to the proximal end portion 104a of the elongate member 104), according to some embodiments. In a state in which the vessel 118 becomes physically disconnected from the catheter sheath device 102 (e.g., as shown, for example, by the sequence of FIG. 6A to FIG. 6B illustrating the disconnection of the vessel 118 at first location 121), the release arm 127a becomes disengaged, which causes engagement of the interlock 127 (e.g., by pivoting interlock jaw 127b (i.e., under the influence of spring-like portion 135) from engagement with the proximal end portion 104a) and prevents or at least restricts, relative movement between the moveable member 110 (without its physically coupled vessel 118) and the proximal end portion 104a of the elongate member 104 (e.g., the moveable member 110 is not configured to move from the first location 121 toward the second location 122 relative to the proximal end portion 104a of the elongate member 104 in absence of the physically coupled vessel 118), according to some embodiments.

In various embodiments, interlock mechanism 127 may be configured to prevent or at least restrict relative movement between the moveable member 110 and the proximal end portion 104a of the elongate member 104 at least in the state in which the second lumen 111 is positioned at the first location 112a relative to the proximal end portion 104a of the elongate member 104. In various embodiments, interlock 127 may be configured to prevent or at least restrict the relative movement between the moveable member 110 and the proximal end portion 104a of the elongate member 104 at a particular location or locations other than the second location 122 in absence of the of a physical coupling of the vessel 118 to the catheter sheath device 102. For example, in some embodiments, interlock 127 may be configured to prevent or at least restrict relative movement between the moveable member 110 and the proximal end portion 104a of the elongate member 104 at the first location 121 in absence of a physical coupling of the vessel 118 to the catheter sheath device 102. In some embodiments, catheter sheath device 102 includes an interlock mechanism, such as interlock 127, configured to restrict or prevent relative movement between the moveable member 110 and the proximal end portion 104a of the elongate member 104 in a state in which the second lumen 111 is positioned at the first location 112a relative to the proximal end portion 104a of the elongate member 104.

The use of interlocks such as interlock 127 may be motivated for different reasons. For example, if the interlock was not present, and the vessel 118 was not physically coupled to catheter sheath device 102, then relative movement between the moveable member 110 and the proximal end portion 104a of the elongate member 104 could position the second lumen 111 in fluidic communication with the first lumen 109 (e.g., at second location 112b). Thus, since the vessel 118 has not been physically coupled to the catheter sheath device 102, undesired fluid (e.g., air) may enter the first lumen 109 from the second lumen 111, since vessel 118 having not been physically coupled to the catheter sheath device 102 cannot act as a barrier to such entry. The presence of undesired fluid in the first lumen 109 may increase patient risk.

In some embodiments, the catheter sheath device 102 may be configured to allow the vessel 118 to be decouplable from the catheter sheath device 102 at least at the first location 121, and the catheter sheath device 102 may be configured to physically prevent or restrict the physically coupled vessel 118 from being decoupled from the catheter sheath device 102 at the second location 122. For example, in various embodiments, catheter sheath device 102 includes a shield 129 (also known as projection 129) that may be sized and positioned to restrict user access to the coupling release member 119*a* at the second location 122 (FIG. 1F), thereby restricting a user from decoupling the vessel 118 from the catheter sheath device 102 at the second location 122. This configuration may be motivated for various reasons. For example, if vessel 118 was to be decoupled from that catheter sheath device 102 at the second location 122, undesired fluid (e.g., air) could enter the first lumen 109 and subsequently increase the potential for patient harm.

As shown at least in FIG. 1E, the physically coupled vessel 118 is at the first location 121 and shield 129 does not restrict user access to coupling release member 119*a*, thereby allowing the vessel 118 to be physically decoupled from the catheter sheath device 102 in this state. Physically decoupling the vessel 118 from the catheter sheath device 102 at first location 121 (as opposed to the second location 122) reduces the potential for undesired fluid (e.g., air) to enter the first lumen 109 and, for example, allows for a safe exchange of catheters at first location 121. It is noted that flushing fluid may be provided into the first lumen 109 via third lumen 114 when the vessel 118 is at the first location 121 or the second lumen 111 is at the first location 112*a* and is not considered detrimental to patient health.

Figure 5:
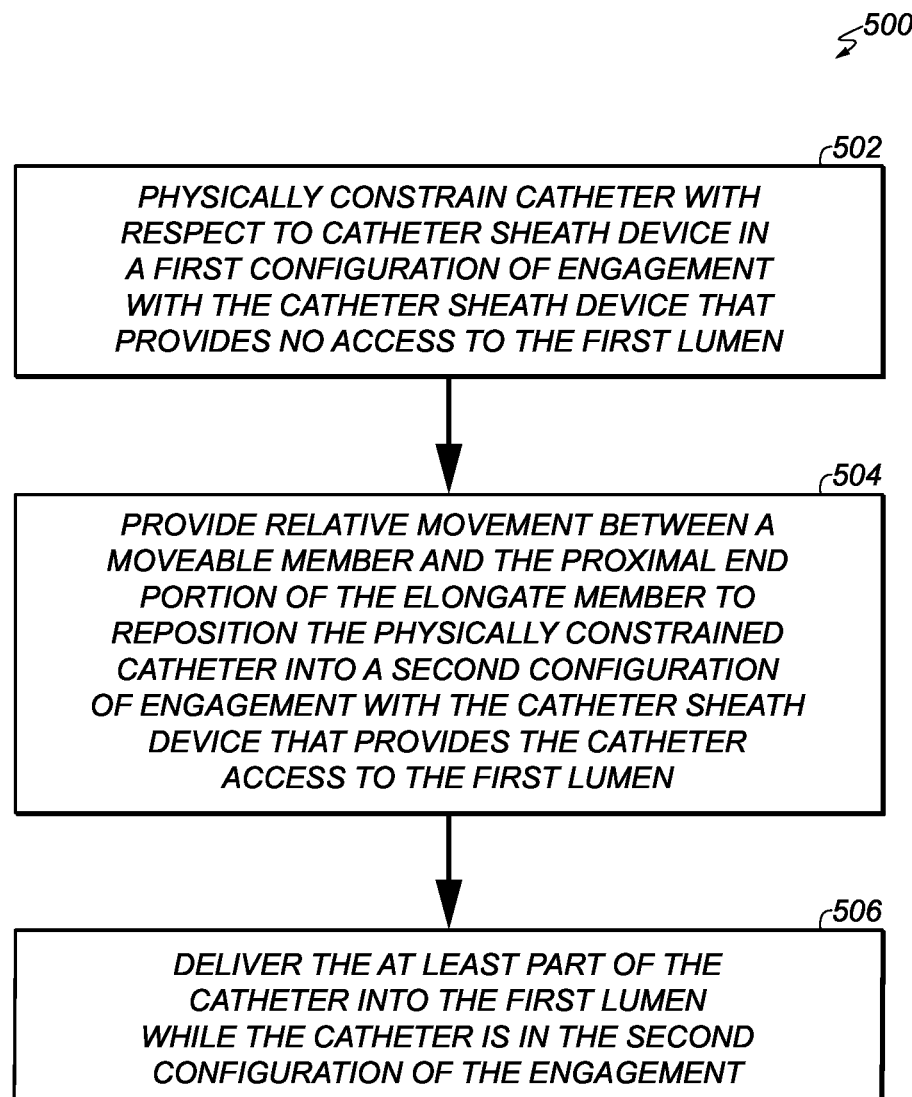
FIG. 5 illustrates a method of delivering at least part of a catheter into a lumen of a catheter sheath device, according to some embodiments of the present invention.

FIG. 5 is a block diagram representing a method 500, according to some embodiments. According to various embodiments, method 500 may include a method of delivering at least part of a catheter (e.g., catheter 120) into a first lumen (e.g., first lumen 109) of a catheter sheath device (e.g., 102). According to some embodiments, the first lumen 109 may be within and extend from a proximal end portion (e.g., proximal end portion 104*a*) of an elongate member (e.g., elongate member 104) of the catheter sheath device 102. According to various embodiments, at least a portion of the elongate member 104 may be configured to be insertable into a body of a patient. It should be noted that various embodiments of the present invention include more or fewer actions and different orderings of actions than those described and illustrated with respect to at least the various blocks of method 500.

Block 502, representing a portion of method 500 according to some embodiments, may include physically constraining the catheter 120 with respect to the catheter sheath device 102 in a first configuration of the engagement with the catheter sheath device 102 that provides the catheter 120 no access to the first lumen 109, according to some embodiments. For example, FIG. 1E shows a first configuration of engagement with the catheter sheath device 102 that provides the catheter 120 no access to the first lumen 109. In FIG. 1E, at least the distal end portion 124*b* of catheter 120 may be physically constrained within the internal cavity 118*a* of vessel 118 due at least in part to the physical coupling of the vessel 118 to the second lumen 111 at the first location 121, which offers the distal end portion 124*b* of catheter 120 no direct access from the first location 121 to the first lumen 109, according to some embodiments. According to some embodiments, the first configuration of engagement may be provided at least in part by the vessel 118 at least in state in which the vessel 118 is physically coupled to the catheter sheath device 102 and at least part of the physically constrained catheter 120 is located in the internal cavity 118*a* of the vessel 118. According to some embodiments, a particular portion of the catheter 120 that is physically constrained in the first configuration of engagement may be denied access to the first lumen 109 in the first configuration of engagement. In some embodiments, a particular portion of the catheter 120 that is physically constrained in the first configuration of engagement may be physically constrained with respect to the moveable member 110.

In some embodiments, the physically constraining the catheter 120 with respect to the catheter sheath device 102 in the first configuration of engagement with the catheters sheath device 102 as per block 502 may include physically constraining relative movement between at least the distal end portion 124*b* of the catheter 120 and the moveable member 110 to be predominantly along a first axis. For example, according to some embodiments associated with FIG. 1E, relative movement between the distal end portion 124*b* of catheter 120 and the moveable member 110 may be physically constrained (e.g., by the physically coupled vessel 118) to be predominantly along first axis 130*a*, although such relative movement may bounded in the first configuration of engagement by at least the entry port of the fourth lumen 126, which, in some embodiments, has a size insufficient to receive at least a portion of the catheter 120. It is noted according to some embodiments, that collet-style valve 118*b* may need to be released sufficiently to release any gripping forces imposed by the physically coupled vessel 118 on the catheter 120 and thereby allow the relative movement along the first axis 130*a*. The first axis 130*a* may be parallel to the longitudinal axis 109*a* of the first lumen 109. In some embodiments, the first axis 130*a* may be collinear with the longitudinal axis 109*a* of the first lumen 109 after the catheter sheath device 102 has been changed from the first configuration of engagement shown, e.g., at least in FIG. 1E, to the second configuration of engagement shown, e.g., at least in FIG. 1F per block 504 discussed below. In some embodiments, the first axis 130*a* may be parallel to, or collinear with, the longitudinal axis 111*a* of the second lumen 111 at least in (a) a state in which the second lumen 111 is positioned at the first location 112*a*, (b) a state in which the second lumen 111 is positioned at the second location 112*b*, or both (a) and (b).

In some embodiments, the physically constraining the catheter 120 with respect to the catheter sheath device 102 as per block 502 may include restricting relative movement between at least a distal end portion 124*b* of the catheter and the moveable member 110 along a second axis (e.g., an axis parallel to axis X-X). For example, the physically coupled vessel 118 and its physical coupling to the second lumen 111 at the first location 121 in the first configuration of engagement may restrict or prevent movement of the distal end portion 124*b* along one or more particular axes other than first axis 130*a*. In some embodiments, the second axis (e.g., an axis parallel to axis X-X) may be perpendicular to a longitudinal axis 109*a* of the first lumen 109. It is noted that, in some embodiments, some lateral play may exist between the distal end portion 124*b* of the catheter 120 and the physically constrained vessel 118 or the moveable member 110. Nonetheless, such play is considered minor and the first configuration of engagement confines relative movement between at least the distal end portion 124*b* of the catheter 120 and the moveable member 110 to be predominantly along the first axis 130*a*. For example, the phrase "predominantly along the first axis 130*a*" may include or allow for some relative movement of the distal end portion 124*b* of the catheter 120 along an axis parallel to axis X-X within the confines of the internal cavity 118a of the vessel 118, according to some embodiments. In this regard, in some embodiments, the physically constraining the catheter 120 with respect to the catheter sheath device 102 in the first configuration of engagement with the catheter sheath device 102 as per block 502 may include physically coupling a fluid-containing vessel (e.g., vessel 118) to the catheter sheath device 102, e.g., by physically coupling the fluid-containing vessel to the moveable member 110. According to some embodiments, at least a portion of the catheter 120 may be physically constrained to move within the fluid-containing vessel (e.g., within the internal cavity 118a of the vessel 118). According to some embodiments, at least a portion of the catheter 120 may be physically constrained to move within the fluid-containing vessel in the first configuration of engagement. In some embodiments, the physically constraining the catheter 120 with respect to the catheter sheath device 102 in the first configuration of engagement with the catheter sheath device 102 as per block 502 may include physically coupling a fluid-containing vessel (e.g., vessel 118) to the moveable member 110. According to some embodiments, at least a portion of the catheter 120 may be physically constrained to move within the fluid-containing vessel. According to some embodiments, at least a portion of the catheter 120 may be physically constrained to move within the fluid-containing vessel in the first configuration of engagement.

In some embodiments, the catheter sheath device 102 may be configured to prevent relative movement between the moveable member 110 and the proximal end portion 104a of the elongate member 104 in absence of the physically constraining the catheter 120 with respect to the catheter sheath device 102 in the first configuration of engagement. For example, an interlock such as interlock 127 (FIG. 1B) may be employed to prevent relative movement between the moveable member 110 and the proximal end portion 104a of the elongate member 104 in absence of the physically constraining the catheter 120 with respect to the catheter sheath device 102 in the first configuration of engagement. In some embodiments, the physically constraining of the catheter 120 with respect to the catheter sheath device 102 may be pursuant to a physical coupling of the vessel 118 to the catheter sheath device 102. However, it may be preferable in other situations to prevent relative movement between the moveable member 110 and the proximal end portion 104a of the elongate member 104. For example, the interlock 127 or other mechanism to prevent such relative movement, may be employed to provide notice to an operator that an operative device, be it the vessel 118 and its included catheter 120, or some other device required by the performance of a particular procedure on a patient, is not fully or otherwise properly connected to the catheter sheath device 102, according to some embodiments. In other words, e.g., an operator may not be able to move the moveable member 110 into its operative state (e.g., at least FIGS. 1D and 1F), due to the interlock 127 or other mechanism, unless the operative device is fully and otherwise properly connected to the catheter sheath device 102, according to some embodiments.

Block 504, representing a portion of method 500 according to some embodiments, may include providing relative movement between a moveable member (e.g., moveable member 110) and the proximal end portion 104a of the elongate member 104 to reposition the physically constrained catheter 120 into a second configuration of engagement with the catheter sheath device 102 that provides the catheter 120 access to the first lumen 109, the moveable member physically coupled to the proximal end portion 104a of the elongate member 104. FIG. 1F shows an example of such a second configuration of engagement with the catheter sheath device 102 that provides the catheter 120 access to the first lumen 109. In some embodiments, the providing relative movement between the moveable member 110 and the proximal end portion 104a of the elongate member 104 to reposition the physically constrained catheter 120 into the second configuration of engagement with the catheter sheath device 102 as per block 504 may include causing the second lumen 111 to overlap at least part of the first lumen 109 as viewed along a viewing direction extending along the longitudinal axis 111a of the second lumen 111. According the various embodiments, the amount of overlap between the second lumen 111 and the first lumen 109 may be sufficient to subsequently permit a delivery of the at least part of the catheter 120 into the first lumen 109 from the second lumen 111. In some embodiments, the providing relative movement between the moveable member 110 and the proximal end portion 104a of the elongate member 104 to reposition the physically constrained catheter 120 into the second configuration of engagement with the catheter sheath device 102 as per block 504 may include providing relative movement between the moveable member 110 and the proximal end portion 104a of the elongate member 104 along second axis (e.g., an axis parallel to axis X-X) that is not parallel with the first axis 130a.

In FIG. 1F, at least the distal end portion 124b of catheter 120 may be physically constrained at a particular location (e.g., second location 121) that offers the distal end portion 124b of catheter 120 access from the particular location to the first lumen 109, according to some embodiments. According to some embodiments, the second configuration of engagement may be provided at least in part by the vessel 118 at least in a state in which the vessel 118 is physically coupled to the catheter sheath device 102 and at least part of the catheter 120 is located in the internal cavity 118a of the physically constrained catheter. According to some embodiments, a particular portion of the catheter 120 that is physically constrained in the second configuration of engagement may be permitted access to the first lumen 109. In some embodiments, a particular portion of the catheter 120 that is physically constrained in the second configuration of engagement may be physically constrained with respect to the moveable member 110.

Block 506, representing a portion of method 500 according to some embodiments, may include delivering the at least part of the catheter 120 into the first lumen 109 in a state in which the catheter 120 is in the second configuration of engagement.

In some embodiments, the delivering the at least part of the catheter 120 into the first lumen 109 in a state in which the catheter 120 is in the second configuration of engagement as per block 506 may include delivering the at least part of the catheter 120 (e.g., at least the distal end portion 124b) into the first lumen 109 from second lumen 111. For example, according to various embodiments, the physically constrained catheter 120 may be physically constrained to be delivered through the second lumen 111, and therefore delivery of the least part of the catheter 120 into the first lumen 109 occurs from or via the second lumen 111 in the state in which the catheter 120 is in the second configuration of engagement (e.g., at least FIG. 1F).

Method 500 may be motivated for different reasons. For example, in some embodiments, the physically constraining the catheter 120 with respect to the catheter sheath device 102 in the first configuration of engagement with the catheter sheath device 102 provides the catheter 120 no access to the first lumen 109 as per block 502 to allow various actions the be performed on the catheter (e.g., flushing or catheter exchange) in a manner that limits particular interactions with the first lumen 109, the particular interactions possibly leading to increased patient risk, such as the risk of introduction of undesired fluid (e.g., air) into the first lumen 109. The providing the relative movement between the moveable member 110 and the proximal end portion 104a of the elongate member 104 to reposition the physically constrained catheter 120 into the second configuration of engagement with the catheter sheath device 102 as per block 504 may advantageously reposition an already-prepared (e.g., flushed or exchanged) catheter 120 at a location in which access to the first lumen 109 is permitted while reducing risk to the patient, such as by the introduction of undesired fluid into first lumen 109 or the catheter 120 during the repositioning.

While some of the embodiments disclosed above are suitable for the flushing of various instruments employed in cardiac procedures, the same or similar embodiments may be used for flushing various instruments used in the treatment or diagnosis or other bodily organs or any bodily lumen, bodily chamber or bodily cavity. Some embodiments may pertain to non-flushing applications, such as irrigation applications.

Subsets or combinations of various embodiments described above can provide further embodiments.

These and other changes may be made to the invention in light of the above-detailed description. In general, in the following claims, the terms used should not be construed to limit the invention to the specific embodiments disclosed in the specification and the claims. In this regard, the invention is not limited by the disclosure, but instead its scope is to be determined entirely by the following claims.

What is claimed is:

1. A catheter sheath device comprising:
an elongate member, at least a portion thereof configured to be insertable into a body of a patient, the elongate member comprising a proximal end portion and a first lumen extending within and extending from the proximal end portion of the elongate member; and
a moveable member physically coupled to the proximal end portion of the elongate member to permit relative movement therebetween,
wherein the catheter sheath device is manipulable into a first configuration of engagement with a catheter, the first configuration of engagement configured to physically constrain the catheter with respect to the catheter sheath device, and the first configuration of engagement configured to provide the catheter no access to the first lumen,
wherein the catheter sheath device is manipulable into a second configuration of engagement with the catheter, the second configuration of engagement configured to provide the catheter with access to the first lumen, and
wherein the moveable member is configured, via being physically coupled to the proximal end portion of the elongate member to and via a relative movement between the moveable member and the proximal end portion of the elongate member, to reposition the physically constrained catheter from the first configuration of engagement into the second configuration of engagement that is configured to provide the catheter access to the first lumen, the first lumen configured to receive at least part of the catheter in the second configuration of engagement.

2. The catheter sheath device of claim 1, wherein the catheter sheath device is configured to prevent relative movement between the moveable member and the proximal end portion of the elongate member in absence of the physically constraining of the catheter with respect to the catheter sheath device in the first configuration of engagement.

3. The catheter sheath device of claim 1, wherein, in the first configuration of engagement, the catheter sheath device is configured to physically constrain the catheter in a manner in which relative movement between at least a distal end portion of the catheter and the moveable member is physically constrained to be predominantly along a first axis.

4. The catheter sheath device of claim 3, wherein the relative movement between the moveable member and the proximal end portion of the elongate member to reposition the physically constrained catheter from the first configuration of engagement into the second configuration of engagement comprises relative movement between the moveable member and the proximal end portion of the elongate member along a second axis that is not parallel with the first axis.

5. The catheter sheath device of claim 3, wherein the first axis is parallel to a longitudinal axis of the first lumen.

6. The catheter sheath device of claim 5, wherein the first axis and the longitudinal axis of the first lumen are colinear in a state in which the catheter sheath device is in the second configuration of engagement with the catheter.

7. The catheter sheath device of claim 3, wherein the moveable member comprises a second lumen, and the first axis is parallel to a longitudinal axis of the second lumen.

8. The catheter sheath device of claim 7, wherein the first lumen is configured to receive at least part of the catheter from the second lumen in a state in which the catheter sheath device is in the second configuration of engagement with the catheter.

9. The catheter sheath device of claim 7, wherein the relative movement between the moveable member and the proximal end portion of the elongate member to reposition the physically constrained catheter from the first configuration of engagement into the second configuration of engagement comprises causing the second lumen to overlap at least part of the first lumen as viewed along a viewing direction extending along the longitudinal axis of the second lumen.

10. The catheter sheath device of claim 1, wherein, in the first configuration of engagement, the catheter is physically constrained with respect to the catheter sheath device in a manner in which relative movement between at least a distal end portion of the catheter and the moveable member is restricted along a second axis.

11. The catheter sheath device of claim 10, wherein the second axis is perpendicular to a longitudinal axis of the first lumen.

12. The catheter sheath device of claim 1,
wherein, in the first configuration of engagement, the catheter sheath device is configured to be physically coupled to a vessel at a first location relative to the proximal end portion of the elongate member, the first configuration of engagement configured to provide a portion of the catheter in an internal cavity of the vessel with no access to the first lumen, and
wherein, in the second configuration of engagement, the catheter sheath device is configured to be physically coupled to the vessel at a second location relative to the proximal end portion of the elongate member, the second location other than the first location, and the second configuration of engagement configured to provide the portion of the catheter in the internal cavity of the vessel with access to the first lumen.

13. The catheter sheath device of claim 12, wherein the vessel is configured to contain fluid in the internal cavity of the vessel, wherein the catheter sheath device is configured to cause the internal cavity of the vessel, in a state in which it is physically coupled at the first location, to be fluidically disconnected from the first lumen, and wherein catheter sheath device is configured to cause the internal cavity of the vessel, in a state in which it is physically coupled at the second location, to be fluidically connected to the first lumen.

14. The catheter sheath device of claim 12, wherein, in the first configuration of engagement, the first lumen is configured to receive fluid from a fluid supply.

15. The catheter sheath device of claim 14, wherein the first lumen is configured to receive the fluid from the fluid supply by at least receiving the fluid through a particular lumen provided in the moveable member, the particular lumen fluidically disconnected from the internal cavity of the vessel.

16. The catheter sheath device of claim 14, wherein catheter sheath device is configured to fluidically disconnect the fluid supply from the internal cavity of the vessel during a time when the first lumen receives the fluid from the fluid supply.

17. The catheter sheath device of claim 12, wherein the catheter sheath device is configured to prevent relative movement between the moveable member and the proximal end portion of the elongate member in absence of a physical coupling of the vessel to the catheter sheath device.

18. The catheter sheath device of claim 12, wherein the catheter sheath device is configured to allow the vessel to be decouplable from the catheter sheath device at least at the first location, and the catheter sheath device is configured to physically restrict the physically coupled vessel from being decoupled from the catheter sheath device at the second location.

19. The catheter sheath device of claim 12, wherein the portion of the catheter is a distal end portion of the catheter, and, in a state in which the physically coupled vessel is at the second location, the catheter sheath device is configured to receive the catheter distal-end-portion-first into the first lumen.

20. The catheter sheath device of claim 12, wherein, in the first configuration of engagement, the internal cavity of the vessel is configured to have fluid located therein.

21. The catheter sheath device of claim 12, wherein, in the second configuration of engagement in which the vessel is physically coupled at the second location, the first lumen is configured to receive the portion of the catheter from the internal cavity of the vessel.

22. The catheter sheath device of claim 21, wherein the portion of the catheter is a distal end portion of the catheter, the distal end portion of the catheter selectively configurable between a delivery configuration in which the distal end portion of the catheter is sized to be deliverable through the first lumen and a deployed configuration in which the distal end portion of the catheter is sized too large to be deliverable through the first lumen, and wherein, in the second configuration of engagement in which the vessel is physically coupled at the second location, the first lumen is configured to receive the distal end portion of the catheter in the delivery configuration from the internal cavity of the physically coupled vessel located at the second location.

23. The catheter sheath device of claim 12, wherein the portion of the catheter is a distal end portion of the catheter, the distal end portion of the catheter selectively configurable between a delivery configuration in which the distal end portion of the catheter is sized to be deliverable through the first lumen and a deployed configuration in which the distal end portion of the catheter is sized too large to be deliverable through the first lumen, and wherein at least the distal end portion of the catheter is configured to be provided in the delivery configuration in the internal cavity of the vessel.

24. The catheter sheath device of claim 12, wherein the portion of the catheter is a distal end portion of the catheter, the distal end portion of the catheter selectively configurable between a delivery configuration in which the distal end portion of the catheter is sized to be deliverable through the first lumen and a deployed configuration in which the distal end portion of the catheter is sized too large to be deliverable through the first lumen, and wherein the internal cavity of the vessel is insufficiently sized to permit the distal end portion of the catheter to be provided therein in the deployed configuration.

* * * * *